United States Patent
Snyder et al.

(10) Patent No.: US 10,954,547 B1
(45) Date of Patent: Mar. 23, 2021

(54) METHODS FOR QUANTIFYING STARCH AND CELLULOSE IN CORN SAMPLES

(71) Applicant: EdeniQ, Inc., Visalia, CA (US)

(72) Inventors: David Scott Snyder, Visalia, CA (US); Prachand Shrestha, Visalia, CA (US)

(73) Assignee: EDENIQ, INC., Visalia, CA (US)

( * ) Notice: Subject to any disclaimer, the term of this patent is extended or adjusted under 35 U.S.C. 154(b) by 213 days.

(21) Appl. No.: 16/230,269

(22) Filed: Dec. 21, 2018

Related U.S. Application Data

(60) Provisional application No. 62/609,146, filed on Dec. 21, 2017.

(51) Int. Cl.
| | | |
|---|---|---|
| *B01D 11/02* | (2006.01) | |
| *C12Q 1/34* | (2006.01) | |
| *G01N 33/487* | (2006.01) | |

(52) U.S. Cl.
CPC ............... *C12Q 1/34* (2013.01); *B01D 11/02* (2013.01); *G01N 33/487* (2013.01); *C12Q 2545/114* (2013.01); *C12Y 302/01004* (2013.01); *C12Y 302/01091* (2013.01)

(58) Field of Classification Search
None
See application file for complete search history.

(56) References Cited

PUBLICATIONS

Ass et al. "Studies on the Homogeneous Acetylation of Cellulose in the Novel Solvent Dimethyl Sulfoxide/Tetrabutylammonium Fluoride Trihydrate" Macromol. Biosci. 2004, 4, 1008-1013 (Year: 2004).*
Gubitosi et al. "On cellulose dissolution and aggregation in aqueous tetrabutylammonium hydroxide" Biomacromolecules 2016, 17, 2873-2881 (Year: 2016).*
Köhler et al. "New Solvents for Cellulose: Dimethyl Sulfoxide/ Ammonium Fluorides" Macromol. Biosci. 2007, 7, 307-314 (Year: 2007).*
Östlund et al. "Dissolution and Gelation of Cellulose in TBAF/ DMSO Solutions: The Roles of Fluoride Ions and Water" Biomacromolecules 2009, 10, 2401-2407 (Year: 2009).*
Zhong et al. "Wheat straw cellulose dissolution and isolation by tetra-n-butylammonium hydroxide" Carbohydrate Polymers 94 (2013) 38-45 (Year: 2013).*
Kostag 2010 "Recent Advances in Solvents for the Dissolution, Shaping and Derivatization of Cellulose: Quaternary Ammonium Electrolytes and their Solutions in Water and Molecular Solvents" Molecules 2018, 23, 511, 38pgs (Year: 2018).*
Banerjee, et al. "Rapid Optimization of Enzyme mixtures for deconstruction of diverse pretreatment/biomass feedstock combinations." Biotechnology for Biofuels, 2010, 3:22, 15 pages.
Chen, et al. "Effect of digestion by pure cellulases on crystallinity and average chain length for bacterial and microcrystalline celluloses", Springer Science + Business Media B.V., Feb. 12, 2007, 11 pages.
Ciolacu, et al. "Amorphous Cellulose—Structure and Characterization". Cellulose Chemistry and Technology, 45 (1-2), 13-21, (2011), 9 pages.
Englyst, et al. "Simplified Method for the Measurement of Total Non-starch Polysaccharides by Gas—Liquid Chromatography of Constituent Sugars as Alditol Acetates", Analyst, Jul. 1984, vol. 109, 6 pages.
Heinze, et al. "Effective preparation of cellulose derivatives in a new simple cellulose solvent", Macromolecular Chemistry and Physics, 201, 627-631 (2000), 5 pages.
Heinze, et al. "Solvents Applied in the Field of Cellulose Chemistry—A Mini Review", Polímeros: Ciência e Tecnologia, vol. 15, n° 2, p. 84-90, 2005, 7 pages.
Jiang, et al. , "Effective Preparation of Bamboo Cellulose Fibers in Quaternary Ammonium/DMSO Solvent", Bio Resources, 11(2), pp. 4536-4549, (2016), 14 pages.
Lee, et al. "Evaluation of Organosolv Processes for the Fractionation and Modification of Corn Stover for Bioconversion", Biotechnology and Bioengineering, vol. XXIX, pp. 572-581 (1987) 0 1987 John Wiley & Sons, Inc., 10 pages.
Parthasarathi, et al. "Activation of lignocellulosic biomass for higher sugar yields using aqueous ionic liquid at low severity process conditions", Biotechnol Biofuels (2016) 9:160, 13, pages.
Sluiter, et al. "Determination of Sugars, Byproducts, and Degradation Products in Liquid Fraction Process Samples", Technical Report, NREL/TP-510-42623, Jan. 2008, 14 pages.
Zhao, et al. "Organosolv pretreatment of lignocellulosic biomass for enzymatic hydrolysis", Oct. 16, 2008 / Revised: Jan. 20, 2009 / Accepted: Jan. 20, 2009 / Published online: Feb. 12, 2009, 13 pages.

\* cited by examiner

*Primary Examiner* — Thane Underdahl
(74) *Attorney, Agent, or Firm* — Kilpatrick Townsend & Stockton LLP

(57) ABSTRACT

Solutions and methods are disclosed for the extraction and quantification of cellulose derived from cellulosic biomass samples. Improved extraction yields and selectivities are provided through the use of an extraction solvent mixture comprising an aprotic solvent such as DMSO, a quaternary ammonium salt such as TBAF, and an quaternary ammonium base such as TBAOH. The extracted cellulose can be optionally precipitated using disclosed precipitation solutions to further improve cellulose purity. Extracted cellulose can be measured by hydrolyzing the cellulose to glucose or cellobiose, or by using disclosed spectrophotometric assays of cellulose-salt complexes.

16 Claims, 4 Drawing Sheets

METHODS FOR QUANTIFYING STARCH AND CELLULOSE IN CORN SAMPLES

CROSS-REFERENCES TO RELATED APPLICATIONS

The present application claims priority from and is a non-provisional application of U.S. Provisional Application No. 62/609,146, entitled "Methods for Quantifying Starch and Cellulose in Corn Samples" filed Dec. 21, 2017 the entire content of which are herein incorporated by reference for all purposes.

BACKGROUND

Biofuels produced from agricultural products provide a potential source for new transportation energy. By using such renewable feedstocks as raw materials, it is believed that fuel and other chemicals can be manufactured in a way that is sustainable, economically viable, and environmentally responsible. An example of a first-generation biofuel is ethanol produced from corn. Corn ethanol is made by extracting and converting the starch found in corn kernels into ethanol using conventional and readily-available technology.

Corn kernel starch, however, is only one component that is available from this biomass feedstock. For example, corn kernels that are used in the manufacture of corn ethanol can comprise approximately 70% starch, 10% fiber, 10% protein, 5% oil, and 5% ash on a dry weight basis. In a conventional dry grind corn ethanol process, the starch is converted nearly quantitatively to glucose via enzymatic hydrolysis, and the glucose is then fermented to ethanol using yeast. The corn oil is extracted and has commercial value as a byproduct. The remaining material, including the fiber, protein, and small amounts of residual starch, is often sold as distillers grains for use as animal feed. This fiber can comprise cellulose, hemicellulose and lignin in roughly equal parts.

The United States Environmental Protection Agency recently approved corn kernel fiber (CKF) as a feedstock for the production of cellulosic ethanol as a second-generation biofuel. As such, an ethanol producer wishing to manufacture cellulosic ethanol for which government credits are available has the option of either separating the CKF from the corn starch for subsequent processing to cellulosic ethanol, or co-processing the CKF and corn starch together to produce a mixture of cellulosic and non-cellulosic ethanol. In the latter case, the producer must be able to quantitatively determine the concentrations of both starch and cellulose that are commingled in relevant process samples in order to demonstrate the production of cellulosic ethanol. Such determination demands techniques for separating and analyzing the cellulose and starch components of cellulosic biomass samples.

BRIEF SUMMARY

In general, provided herein are methods and solutions that are characterized by the extraction and quantification of cellulose found in biomass samples. One provided method of detecting the amount of cellulose in a cellulosic biomass sample includes contacting the cellulosic biomass sample with a solvent mixture, thereby extracting cellulose from the cellulosic biomass sample into the solvent mixture. The solvent mixture comprises a polar aprotic solvent, a quaternary ammonium salt, and a quaternary ammonium base. The method further comprises detecting the amount of extracted cellulose. In some embodiments, the polar aprotic solvent is dimethyl sulfoxide (DMSO). In some embodiments, the quaternary ammonium salt is tetrabutylammonium fluoride (TBAF). In some embodiments, the quaternary ammonium base is tetrabutylammonium hydroxide (TBAOH).

In some embodiments, the concentration of the quaternary ammonium salt in the solvent mixture is from 10 mg/mL to 500 mg/mL, e.g., from 50 mg/mL to 500 mg/mL. In some embodiments, the concentration of the quaternary ammonium base in the solvent mixture is from 1 mg/mL to 1500 mg/mL, e.g., from 10 mg/mL to 1500 mg/mL. In some embodiments, the mass ratio of the quaternary ammonium salt to the quaternary ammonium base is from 0.05 to 15. In some embodiments, the amount of the solvent mixture contacting the cellulosic biomass sample is from 1 mL to 50 mL per gram of cellulosic biomass.

In some embodiments, the detecting comprises converting the extracted cellulose into glucose, measuring a concentration of glucose converted from the extracted cellulose, and transforming the measured concentration of glucose to a calculated concentration of extracted cellulose. In some embodiments, the converting of the extracted cellulose into glucose comprises treating the extracted cellulose with one or more saccharifying enzymes. In some embodiments, the converting of the extracted cellulose into glucose comprises submitting the extracted cellulose to acid hydrolysis. In some embodiments, the method comprises, prior to the converting of the extracted cellulose into glucose, selectively precipitating the extracted cellulose from the solvent mixture.

In some embodiments, the detecting comprises converting the extracted cellulose into cellobiose, measuring a concentration of cellobiose converted from the extracted cellulose, and transforming the measured concentration of cellobiose to a calculated concentration of extracted cellulose. In some embodiments, the converting of the extracted cellulose into cellobiose comprises treating the extracted cellulose with one or more saccharifying enzymes. In some embodiments, the method comprises, prior to the converting of the extracted cellulose into cellobiose, selectively precipitating the extracted cellulose from the solvent mixture.

In some embodiments, the contacting of the cellulosic biomass sample with the solvent mixture comprises forming cellulose-quaternary ammonium salt complexes in the solvent mixture, and the detecting comprises measuring a concentration of cellulose-quaternary ammonium salt complex in the solvent mixture, and transforming the measured concentration of cellulose-quaternary ammonium salt complex to a calculated concentration of extracted cellulose. In some embodiments, the measuring of the concentration of cellulose-quaternary ammonium salt complex comprises a spectroscopic quantification of the cellulose-quaternary ammonium salt complex.

In some embodiments, the method further comprises pretreating the cellulosic biomass sample prior to extracting cellulose from the cellulosic biomass sample into the solvent mixture. In some embodiments, the pretreating comprises contacting the cellulosic biomass sample with a biomass swelling solution. In certain aspects, the biomass swelling solution comprises between 3% and 30% (weight/volume) of one or more metal hydroxides. In some embodiments, the pretreating comprises contacting the cellulosic biomass sample with a xylanase solution. In certain aspects, the xylanase solution comprises an endo-1,4-beta-xylanase, a beta-xylosidase, an arabinofuranosidase, or a combination thereof. In some embodiments, the pretreating comprises contacting the cellulosic biomass solution with an extraction solution comprising a transition metal amine complex. In certain aspects, the transition metal amine complex comprises nitren. In some embodiments, the pretreatment comprises contacting the cellulosic biomass sample with a peracetic acid solution. In certain aspects, upon contacting the biomass sample with the peracetic acid solution, the concentration (weight/volume) of peracetic acid in the combined mixture is from 3% to 33%. In some embodiments, the pretreatment comprises contacting the cellulosic biomass sample with a solution comprising ethanol. In certain aspects, upon contacting the cellulosic biomass sample with the ethanol solution, the volume ratio of ethanol to the biomass sample is from 5 to 50.

Also provided is a cellulosic extraction solution comprising a cellulosic biomass sample and a solvent mixture. The solvent mixture comprises a polar aprotic solvent, a quaternary ammonium salt, and a quaternary ammonium base. In some embodiments, the polar aprotic solvent is DMSO. In some embodiments, the quaternary ammonium salt is TBAF. In some embodiments, the quaternary ammonium base is TBAOH. In some embodiments, the concentration of the quaternary ammonium salt in the solvent mixture rages 10 mg/mL to 500 mg/mL, e.g., from 50 mg/mL to 500 mg/mL. In some embodiments, the concentration of the quaternary ammonium base in the solvent mixture is from 1 mg/mL to 1500 mg/mL, e.g., from 10 mg/mL to 1500 mg/mL. In some embodiments, the mass ratio of the quaternary ammonium salt to the quaternary ammonium base in the solvent mixture is from 0.05 to 15. In some embodiments, the amount of the solvent mixture relative to the cellulosic biomass sample is from 1 mL to 50 mL per gram of cellulosic biomass.

Also provided is a method of detecting the amount of cellulose in a cellulosic biomass sample. The method comprises contacting the cellulosic biomass sample with a solvent mixture comprising a polar aprotic solvent and a quaternary ammonium salt, thereby extracting cellulose from the cellulosic biomass sample into the solvent mixture, and thereby forming cellulose-quaternary ammonium salt complexes in the solvent mixture. The method further comprises measuring a concentration of cellulose-quaternary ammonium salt complexes in the solvent mixture. The method further comprises transforming the measured concentration of cellulose-quaternary ammonium salt complexes to a calculated concentration of extracted cellulose.

In some embodiments, the polar aprotic solvent is DMSO. In some embodiments, the quaternary ammonium salt comprises TBAF and tetrabutylammonium iodide (TBAI). In some embodiments, the concentration of the quaternary ammonium salt in the solvent mixture is from 10 mg/mL to 500 mg/mL, e.g., from 50 mg/mL to 500 mg/mL. In some embodiments, the amount of the solvent mixture contacting the cellulosic biomass sample is from 1 mL to 50 mL per gram of cellulosic biomass. In some embodiments, the measuring comprises a spectroscopic quantification of the cellulose-quaternary ammonium salt complex concentration.

DETAILED DESCRIPTION

Figure 1:
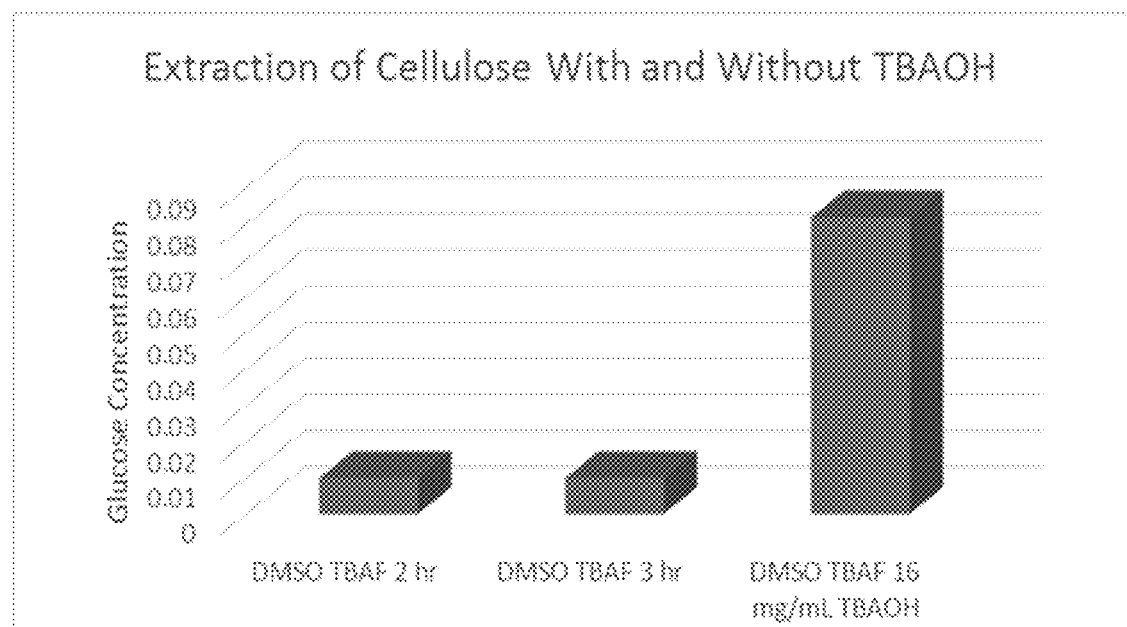
FIG. 1 is a graph of concentrations of glucose converted from cellulose extracted using various solvent mixtures and extraction times.

The inventors have discovered extraction solvents and methods that are advantageous in separating and quantifying cellulose, starch, and other saccharide components of a cellulosic biomass sample. It is beneficial for the cellulose of a biomass sample to be isolated from the starch and glucose from the sample. Several methods for quantifying cellulose in a biomass sample involve converting the cellulose to simpler sugars such as monosaccharides and/or disaccharides, and then assaying these sugars to determine the amount of cellulose from which they originated. When using these assays, if the cellulose is not isolated from starch or other saccharides in the initial biomass sample, then it can be difficult to later ascertain what portion of the simpler sugars is derived from the cellulose, and what portion is derived from the starch or other saccharides also present in the original biomass sample.

This difficulty in distinguishing starch and cellulose commingled in the same sample arises partially because starch and cellulose are both homopolymers of glucose, differentiated by the bond geometries between glucose monomer units (i.e., $\beta(1,4)$ bond geometries for cellulose and $\alpha(1,4)$ and $\alpha(1,6)$ bond linkages for starch). Moreover, both starch and cellulose polymers can be present in a biomass sample in various crystalline and amorphous forms, making separations difficult. Also, the variability in crystal structures of the polymers makes spectroscopic analyses of the cellulose-starch mixture difficult due to line broadening. The use of acid hydrolysis to degrade cellulose to glucose monomeric units also hydrolyzes starch, preventing differentiation using this approach alone. Alternatively, the use of conventional mixtures of cellulolytic enzymes to hydrolyze cellulose to glucose also has difficulty in selectively preserving starch, can suffer from slow reaction velocities, and can be subject to interfering side reactions.

The inventors have now discovered extraction mixtures having particular compositions that are capable of extracting cellulose from cellulosic biomass samples at a high efficiency. The provided extraction solvent mixtures have improved performances relative to conventional solvent mixtures in extracting cellulose from samples in which the cellulose is present in a wide range of concentrations relative to starch and other sample components. The use of the provided extraction solvent mixtures in methods along with cellulose hydrolysis procedures allows for cellulose quantification with the precision, accuracy, and reproducibility required, for example, for an analytical report characterizing a biomass sample. Hydrolysis procedures have also been developed that utilize particular incubation times and combinations of enzymes found to give improved selectivity towards cellulose and improved stability and activity within the solvent extraction mixture. The extractions can also be combined with selective precipitations using particular compositions found to preferentially precipitate cellulose rather than starch or other saccharides. These precipitation solution compositions are designed to displace the fluoride ion from cellulose in solution, causing cellulose to crash out of the solution while permitting starch to remain dissolved. Moreover, a new colorimetric assay is described for the direct quantification of cellulose complexes within an extraction solution.

I. CELLULOSE EXTRACTION SOLUTIONS

One provided cellulose extraction solution comprises a cellulosic biomass sample and a solvent mixture, wherein the solvent mixture includes a polar aprotic solvent and a quaternary ammonium salt. In some embodiments, the solvent mixture consists essentially of a polar aprotic solvent and a quaternary ammonium salt. In some embodiments, the solvent mixture consists of a polar aprotic solvent and a quaternary ammonium salt. The solvent mixture can also include an organic base. In some embodiments, the solvent mixture comprises a polar aprotic solvent, a quaternary ammonium salt, and an organic base. In some embodiments, the solvent mixture consists essentially of a polar aprotic solvent, a quaternary ammonium salt, and an organic base. In some embodiments, the solvent mixture consists of a polar aprotic solvent, a quaternary ammonium salt, and an organic base.

As used herein, the term "cellulose" refers to a homopolymer of β(1-4) linked D-glucose units that form a linear chain. Cellulose can contain several hundred to several thousand or more glucose units, making cellulose a polysaccharide. Cellulose is found in many natural products, such as the cell walls of plants, and thus is present in wood, grasses, pulp, and cotton, among other materials. As used herein, the term "hemicellulose" refers to a heteropolymer containing different saccharide units, such as, but not limited to, xylose, mannose, galactose, rhamnose, and arabinose. Hemicellulose forms a branched polymer with several hundred to several thousand sugar units. Hemicellulose can include both pentose and hexose sugars. As used herein, the term "cellulosic" refers to any material comprising cellulose, and optionally also comprising hemicellulose.

As used herein, the terms "biomass", "biomass feedstock", and "biomass sample" refer to any material comprising cellulosic material, lignocellulosic material, whole grains, starches, inulin, or any other type of structural carbohydrate. Examples of biomass include agricultural products and waste products such as but not limited to grains, e.g., corn, corn kernel fiber, wheat, and barley; sugarcane; corn stover, corn cobs, tubers, Jerusalem artichoke, stalks, and/or other inedible waste parts of food plants; food waste; grasses such as switchgrass, *miscanthus*, and reed canarygrass; and forestry biomass, such as wood, paper, board, and waste wood products. As used herein, the term "lignocellulosic" refers to any material comprising both lignin and cellulose, and optionally also comprising hemicellulose and mixed-linkage plant cell wall beta-glucans. Thus, lignocellulosic materials comprise a subset of cellulosic materials representing those cellulosic materials that also comprise lignin.

The biomass samples described herein can be obtained from cellulosic or lignocellulosic plants such as, but not limited to, grains such as corn and milo (also known as grain sorghum). The samples can be obtained from various stages in a corn ethanol manufacturing process, such as post-liquefied corn mash, samples after fermentation (e.g., beer and Distiller's dried grains with solubles (DDGS)), whole stillage, thin stillage, and syrup. In some embodiments, the biomass sample has been subjected to a pretreatment process. In some embodiments, the biomass is not been pretreated prior to addition to the cellulosic extraction solution.

As used here, the term "pretreatment" refers to the treatment of biomass with physical, chemical, or biological means, or any combination thereof, to render the biomass more susceptible to hydrolysis by, for example, saccharification enzymes. Pretreatment can comprise treating the biomass with one or more of elevated pressures, elevated temperatures, enzymes and chemical compounds. Pretreatment can further comprise physically mixing and/or milling the biomass in order to reduce the size of the biomass particles, change its pore size distribution, and/or disrupt the structural components or microstructure of the biomass. Devices that are useful for physical pretreatment of biomass include, for example, hammer mills, shear mills, cavitation mills, colloid mills, ball mills, end mills, grinders, crushers, plate mills, disk mills, or other high-shear mills used to grind, cut, shear, shred, fiberize, pulverize, crack, rub, curl, fluff, twist, hill, blend, or refine the biomass. The pretreatment process can be accomplished with the biomass in the dry, moist, or wet state and at various pressures and temperatures. An exemplary colloid mill is the CELLUNATOR™ (Edeniq, Visalia, Calif.). Reduction of particle size through pretreatment is described in, for example, International Patent Application Publication No. WO 2010/025171, which is incorporated by reference herein in its entirety. As used herein, the term "pretreated biomass" refers to biomass that has been subjected to pretreatment to render the biomass more susceptible to hydrolysis. One example of pretreated biomass is post-liquefied corn mash, which is corn slurry that has been heated and enzymatically treated prior to fermentation during the production of ethanol. Examples of pretreatment materials and methods suitable for use with the processes and solutions disclosed herein are described in further detail below.

As used herein, the term "hydrolysis" refers to the breaking of glycosidic bonds in polysaccharides to yield simple monomeric and/or oligomeric sugars. For example, hydrolysis of cellulose can produce the six-carbon ($C_6$) sugar glucose, whereas hydrolysis of hemicellulose can produce the five-carbon ($C_5$) sugars xylose and arabinose. Hydrolysis can be accomplished by acid treatment or by treatment with enzymes that include, but are not limited to, amylase, cellulase, beta-glucosidase, cellobiohydrolase, pullulanase, endoglucanase, exoglucanase, xylanase, glucoamylase, inulinase, and others, as well as mixtures or cocktails including any subset of these enzymes or related enzymatic domains.

The cellulosic biomass sample is generally provided in a wet state as an initial biomass sample having a solids content and a water content. The total solids content of the initial cellulosic biomass sample can be measured, for example, according to the Laboratory Analytical Procedure (LAP) of the National Renewable Energy Laboratory (NREL) Technical Report NREL/TP-510-42621. The initial cellulosic biomass sample can have, for example, a total solids content that is from 5 wt % to 95 wt %, e.g., from 5 wt % to 59 wt %, from 14 wt % to 68 wt %, from 23 wt % to 77 wt %, from 32 wt % to 86 wt %, or from 41 wt % to 95 wt %. The initial cellulosic biomass sample can have a total solids content from 50 wt % to 90 wt %, e.g., from 50 wt % to 74 wt %, from 54 wt % to 78 wt %, from 58 wt % to 82 wt %, from 62 wt % to 86 wt %, or from 66 wt % to 90 wt %. In terms of upper limits, the initial cellulosic biomass sample can have a total solids content less than 95 wt %, e.g., less than 90 wt %, less than 86 wt %, less than 82 wt %, less than 78 wt %, less than 74 wt %, less than 70 wt %, less than 66 wt %, less than 62 wt %, less than 58 wt %, less than 54 wt %, less than 50 wt %, less than 41 wt %, less than 32 wt %, less than 23 wt %, or less than 14 wt %. In terms of lower limits, the initial cellulosic biomass sample can have a total solids content greater than 5 wt %, e.g., greater than 14 wt %, greater than 23 wt %, greater than 32 wt %, greater than 41 wt %, greater than 50 wt %, greater than 54 wt %, greater than 58 wt %, greater than 62 wt %, greater than 66 wt %, greater than 70 wt %, greater than 74 wt %, greater than 78 wt %, greater than 82 wt %, or greater than 86 wt %.

In some embodiments, the initial biomass sample is dried prior to addition to the cellulosic extraction solution. The biomass sample can be dried using a drying oven. The biomass sample can be dried using a microwave oven. In some embodiments, the biomass sample is dried by lyophilization.

The amount of the solvent mixture relative to the cellulosic biomass sample in the cellulose extraction solution can be measured in terms of solvent mixture volume per gram of initial wet cellulosic biomass. The amount of the solvent mixture relative to the cellulosic biomass sample in the cellulose extraction solution can, for example, be from 1 mL/g to 50 mL/g, e.g., from 1 mL/g to 30 mL/g, from 5 mL/g to 35 mL/g, from 10 mL/g to 40 mL/g, from 15 mL/g to 45 m/g, or from 20 mL/g to 50 mL/g. In terms of upper limits, the amount of the solvent mixture relative to the cellulosic biomass sample can be less than 50 mL/g, e.g., less than 45 mL/g, less than 40 mL/g, less than 35 mL/g, less than 30 mL/g, less than 25 mL/g, less than 20 mL/g, less than 15 mL/g, less than 10 mL/g, or less than 5 mL/g. In terms of lower limits, the amount of the solvent mixture relative to the cellulosic biomass sample can be greater than 1 mL/g, e.g., greater than 5 mL/g, greater than 10 mL/g, greater than 15 mL/g, greater than 20 mL/g, greater than 25 mL/g, greater than 30 mL/g, greater than 35 mL/g, greater than 40 mL/g, or greater than 45 mL/g.

As used herein, the term "polar aprotic solvent" refers to a solvent that lacks an acidic hydrogen. Polar aprotic solvents generally are characterized by intermediate or high dielectric constants and dipole moments. Polar aprotic solvents also can be used to dissolve salts, including quaternary ammonium salts. Examples of polar aprotic solvents include, but are not limited to, hexamethylphosphoroamide (HMPA), N-methylpyrrolidone (NMP), tetrahydrofuran (THF), ethyl acetate (EtOAc), acetone, dimethylformamide (DMF), acetonitrile (MeCN), dimethyl sulfoxide (DMSO), and propylene carbonate (PC). In some embodiments, the polar aprotic solvent of the solvent mixture is DMSO.

As used herein, the term "quaternary ammonium salt" refers to a salt of a positively charged polyatomic ion having the structure $NR4^+$, wherein R is alkyl or aryl. As used herein, the term "alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl groups can be substituted or unsubstituted. As used herein, the term "aryl" refers to an aromatic ring system having any suitable number of ring atoms and any suitable number of rings. Aryl groups can include any suitable number of ring atoms, such as 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted.

Examples of quaternary ammonium salts include, but are not limited to, 3,6-diamino-10-methylacridin-10-ium chloride, N-methyl-N,N,N-trioctylammonium chloride, (4-amino-4-oxo-3,3-diphenylbutyl)-ethyl-dimethylazanium bromide, N,N,N-trimethyldocosan-1-aminium chloride, N-alkyl-N-benzyl-N,N-dimethylammonium chloride, N-benzyl-N,N-dimethyl-2-{2-[4-(2,4,4-trimethylpentan-2-yl)phenoxy]ethoxy}ethanaminium chloride, benzyl-dodecyl-dimethylammonium bromide, N-benzyl-N,N-bis(2-hydroxyethyl)dodecan-1-aminium chloride, benzyltrimethylammonium fluoride, (1-ethoxy-1-oxohexadecan-2-yl)-trimethylazanium bromide, benzylhexadecyldimethylazanium chloride, hexadecyl-trimethyl-ammonium bromide, hexadecyl-trimethylammonium chloride, (2-hydroxyethyl)trimethylammonium chloride, 1,1'-decane-1,10-diylbis(4-amino-2-methylquinolinium) decyl]-2-methyl-4-quinolin-1-iumamine dichloride, didecyldimethylammonium chloride, N,N-dimethyl-N-octadecyloctadecan-1-aminium chloride, 3-hexyl-2-[3-(3-hexyl-2(3H)benzoxazolylidene)-1-propenyl]benzoxazolium iodide, 6,7-dihydrodipyrido[1,2-a:2',1'-c]pyrazinediium dibromide, 3-ethyl-2-[5-(3-ethyl-2-benzothiazolinylidene)-1,3-pentadienyl]-benzothiazolium iodide, 3,8-diamino-5-ethyl-6-phenylphenanthridinium bromide, 10,10'-(6,22-dioxo-11,14,17-trioxa-7,21-diazaheptacosane-1,27-diyl)bis(3,6-bis(dimethylamino)acridin-10-ium) iodide, 5,5'-(6,22-dioxo-11,14,17-trioxa-7,21-diazaheptacosane-1,27-diyl)bis (3,8-diamino-6-phenylphenanthridin-5-ium) iodide, 10-methyl-9-(10-methylacridin-10-ium-9-yl)acridin-10-ium dinitrate, 8-methyltropinium bromide 2-propylvalerate, N-octyl-1-[10-(4-octyliminopyridin-1-yl)decyl]pyridin-4-imine dihydrochloride, 1-[(2-cyclohexyl-2-phenyl-1,3-dioxolan-4-yl)methyl]-1-methylpiperidin-1-ium iodide, 1-(3-chloroallyl)-3,5,7-triaza-1-azoniaadamantane chloride, [9-(2-carboxyphenyl)-6-diethylamino-3-xanthenylidene]-diethylammonium chloride, 1-(chloromethyl)-4-fluoro-1,4-diazoniabicyclo[2.2.2]octane ditetrafluoroborate, benzyldimethyloctadecylazanium chloride, tetra-n-butylammonium bromide, tetra-n-butylammonium fluoride, tetrabutylammonium hexafluorophosphate, N,N,N-tributyl-1-butanaminium tribromide, tetraethylammonium bromide, N,N,N,N-tetraethylammonium chloride, N,N,N-triethylethanaminium iodide, tetramethylazanium chloride, tetramethylammonium pentafluoridoxenonate, tetraoctylammonium bromide, tetrapropylammonium perruthenate, 4-(3,6-dimethyl-1,3-benzothiazol-3-ium-2-yl)-N,N-dimethylaniline chloride, and N-{2-[(4-Methoxybenzyl)(pyrimidin-2-yl)amino]ethyl}-N,N-dimethylhexadecan-1-aminium bromide. In some embodiments, the quaternary ammonium salt is a tributylammonium salt. In some embodiments, the quaternary ammonium salt is a fluoride salt. In some embodiments, the quaternary ammonium salt is tetrabutylammonium fluoride (TBAF).

The concentration of the quaternary ammonium salt in the solvent mixture can, for example, be from 10 mg/mL to 500 mg/mL, e.g., from 10 mg/mL to 105 mg/mL, from 15 mg/mL to 155 mg/mL, from 20 mg/mL to 230 mg/mL, from 30 mg/mL to 340 mg/mL, or from 50 mg/mL to 500 mg/mL. The concentration of the quaternary ammonium salt in the solvent mixture can be from 50 mg/mL to 200 mg/mL, from 65 mg/mL to 250 mg/mL, from 80 mg/mL to 315 mg/mL, from 100 mg/mL to 400 mg/mL, or from 125 mg/mL to 500 mg/mL. In terms of upper limits, the concentration of the quaternary ammonium salt in the solvent mixture can be less than 500 mg/mL, e.g., less than 400 mg/mL, less than 315 mg/mL, less than 250 mg/mL, less than 200 mg/mL, less than 150 mg/mL, less than 125 mg/mL, less than 100 mg/mL, less than 80 mg/mL, less than 65 mg/mL, less than 50 mg/mL, less than 30 mg/mL, less than 20 mg/mL, or less than 15 mg/mL. In terms of lower limits, the concentration of the quaternary ammonium salt in the solvent mixture can be greater than 10 mg/mL, e.g., greater than 15 mg/mL, greater than 20 mg/mL, greater than 30 mg/mL, greater than 40 mg/mL, greater than 50 mg/mL, greater than 65 mg/mL, greater than 80 mg/mL, greater than 100 mg/mL, greater than 125 mg/mL, greater than 150 mg/mL, greater than 200 mg/mL, greater than 250 mg/mL, greater than 315 mg/mL, or greater than 400 mg/mL.

In some embodiments, the solvent mixture includes an organic base. In some embodiments, the organic base of the solvent mixture is a proton acceptor. Examples of proton accepting organic bases include, but are not limited to, pyridine, methyl amine, imidazole, benzimidazole, triethylamine, and histidine. In some embodiments, the organic base is a hydroxide donor. Examples of hydroxide donating organic bases include, but are not limited to, tetramethylammonium hydroxide, tetrabutylammonium hydroxide, and choline hydroxide. In some embodiments, the organic base is selected to be a sterically bulky molecule having a structure that fits within the chair configuration of the cellulose sugar moieties, interacting with the hydrophobic portions of the cellulose polymer, and at least partially blocking other cellulose interactions. In some embodiments, the organic base is a quaternary ammonium base having the structure $NR4^+OH^-$, wherein R is alkyl or aryl as described above. In some embodiments, the organic base of the solvent mixture is tetrabutylammonium hydroxide (TBAOH).

The concentration of the organic base in the solvent mixture can, for example, be from 1 mg/mL to 1500 mg/mL, e.g., from 1 mg/mL to 80 mg/mL, from 2 mg/mL to 165 mg/mL, from 4 mg/mL to 345 mg/mL, from 9 mg/mL to 720 mg/mL, or from 20 mg/mL to 1500 mg/mL. The concentration of the organic base in the solvent mixture can be from 10 mg/mL to 1500 mg/mL, e.g., from 10 mg/mL to 200 mg/mL, from 15 mg/l to 330 mg/1, from 25 mg/mL to 550 mg/mL, from 45 mg/mL to 910 mg/mL, or from 75 mg/mL to 1500 mg/mL. In terms of upper limits, the concentration of the organic base in the solvent mixture can be less than 1500 mg/mL, e.g., less than 910 mg/mL, less than 550 mg/mL, less than 330 mg/mL, less than 200 mg/mL, less than 130 mg/mL, less than 75 mg/mL, less than 45 mg/mL, less than 25 mg/mL, less than 15 mg/mL, less than 9 mg/mL, less than 4 mg/mL, or less than 2 mg/mL. In terms of lower limits, the concentration of the organic base in the solvent mixture can be greater than 1 mg/mL, e.g., greater than 2 mg/mL, greater than 4 mg/mL, greater than 9 mg/mL, greater than 10 mg/mL, greater than 15 mg/mL, greater than 25 mg/mL, greater than 45 mg/mL, greater than 75 mg/mL, greater than 130 mg/mL, greater than 200 mg/mL, greater than 330 mg/mL, greater than 550 mg/mL, or greater than 910 mg/mL.

The mass ratio of the quaternary ammonium salt to the organic base in the solvent mixture can, for example, be from 0.05 to 15, e.g., from 0.05 to 9, from 1.5 to 10.5, from 3 to 12, from 4.5 to 13.5, or from 6 to 15. In terms of upper limits, the mass ratio of the quaternary ammonium salt to the organic base can be less than 15, e.g., less than 13.5, less than 12, less than 10.5, less than 9, less than 7.5, less than 6, less than 4.5, less than 3, or less than 1.5. In terms of lower limits, the mass ratio of the quaternary ammonium salt to the organic base can be greater than 0.05, e.g., greater than 1.5, greater than 3, greater than 4.5, greater than 6, greater than 7.5, greater than 9, greater than 10.5, greater than 12, or greater than 13.5.

II. CELLULOSE EXTRACTION METHODS

Also provided are extraction methods using the provided cellulose extraction solutions and solvent mixtures as described above. Optionally, the extraction methods can also include a precipitation mixture as described below. In general, if any subsequent hydrolysis or analysis operation is tolerant of the extraction solution composition, extraction yield, and extraction selectivity afforded by the extraction step alone, then the precipitation step can be omitted. Otherwise, the precipitation step can be used to further remove the extracted cellulose from any co-extracted starch or other saccharides, or from solvents or other extraction mixture components that could interfere with downstream enzymatic, biological, or chemical reactions.

A. Extraction

The cellulose extraction methods include providing a cellulosic biomass sample and a solvent mixture. The cellulosic biomass sample can be any of the samples as described above. The solvent mixture can be any of the solvent mixtures as described above. In some embodiments, the cellulosic biomass sample is provided in an initial wet state having a total solids content and a water content. In some embodiments, the cellulosic biomass sample is dried by, for example, lyophilization, to reduce the water content below that of the initial wet state of the cellulosic biomass sample. In some embodiments, the solvent mixture comprises a polar aprotic solvent, a quaternary ammonium salt, and an organic base. In some embodiments, the solvent comprises DMSO, TBAF, and TBAOH.

The cellulose extraction methods involve contacting the cellulosic biomass sample with the solvent mixture. In some embodiments, the cellulosic biomass sample is dried as described above prior to contacting with the solvent mixture. Once the cellulosic biomass sample and the solvent mixture have been combined with one another, they are allowed to remain in contact for an extraction time at an extraction temperature.

The extraction time can, for example, be from 5 minutes to 360 minutes, e.g., from 5 minutes to 65 minutes, from 10 minutes to 100 minutes, from 15 minutes to 150 minutes, from 20 minutes to 240 minutes, or from 30 minutes to 360 minutes. In terms of upper limits, the extraction time can be less than 360 minutes, e.g., less than 240 minutes, less than 150 minutes, less than 100 minutes, less than 65 minutes, less than 45 minutes, less than 30 minutes, less than 20 minutes, less than 15 minutes, or less than 10 minutes. In terms of lower limits, the extraction time can be greater than 5 minutes, e.g., greater than 10 minutes, greater than 15 minutes, greater than 20 minutes, greater than 30 minutes, greater than 45 minutes, greater than 65 minutes, greater than 100 minutes, greater than 150 minutes, or greater than 240 minutes.

The extraction temperature can, for example, be from 20° C. to 100° C., e.g., from 20° C. to 68° C., from 28° C. to 76° C., from 36° C. to 84° C., from 44° C. to 92° C., or from 52° C. to 100° C. In terms of upper limits, the extraction temperature can be less than 100° C., less than 92° C., less than 84° C., less than 76° C., less than 68° C., less than 60° C., less than 52° C., less than 44° C., less than 36° C., or less than 28° C. In terms of lower limits, the extraction temperature can be greater than 20° C., e.g., greater than 28° C., greater than 36° C., greater than 44° C., greater than 52° C., greater than 60° C., greater than 68° C., greater than 76° C., greater than 84° C., or greater than 92° C.

The yield of cellulose extracted from the initial cellulosic biomass sample can, for example, be from 50% to 100%, e.g., from 50% to 80%, from 55% to 85%, from 60% to 90%, from 65% to 95%, or from 70% to 100%. In terms of lower limits, the yield of extracted cellulose can be greater than 50%, greater than 55%, greater than 60%, greater than 65%, greater than 70%, greater than 75%, greater than 80%, greater than 85%, greater than 90%, or greater than 95%.

B. Precipitation

The cellulose isolation method can optionally include, subsequent to the extraction as described above, one or more steps to further isolate the extracted cellulose from any extracted starch and/or other saccharides. The cellulose isolation method can include, for example, a precipitation step to selectively precipitate the extracted cellulose from the solvent mixture, while preserving starch and/or other saccharides in solution. The parameters of such a precipitation step are therefore selected to increase the yield of cellulose precipitation (i.e., the percentage of extracted cellulose in the solvent mixture that is induced to precipitate) and the selectivity of cellulose precipitation (i.e., the ratio of the cellulose precipitation yield to the precipitation yields of starch and/or other saccharides). In some embodiments, the precipitation step affords another advantage of removing the cellulose from the solvent mixture, allowing, for example, saccharification enzymes less tolerant to organic solvent to be used.

The selective cellulose precipitation can be induced with the addition of a precipitation solution to the extraction solvent mixture. In some embodiments, the precipitation solution is a salt solution. If a purely aqueous salt solution is used to induce precipitation, the selectivity of cellulose precipitation can suffer, as purely aqueous salt solutions can be effective in inducing starch to precipitate out of the solvent mixture. In some embodiments, the precipitation solution comprises one or more organic solvents. In some embodiments, the precipitation solution comprises an aprotic organic solvent. In some embodiments, the precipitation solution comprises DMSO.

The salt of the precipitation solution can be selected for its solubility in non-aqueous solutions. The salt can be, for example, a perchlorate, e.g., ammonium perchlorate, potassium perchlorate, or sodium perchlorate. In some embodiments, the precipitation solution comprises sodium perchlorate. The concentration of the salt in the precipitation solution can, for example, be from 15 mg/mL to 150 mg/mL, e.g., from 15 mg/mL to 60 mg/mL, from 20 mg/mL to 75 mg/mL, from 25 mg/mL to 95 mg/mL, from 30 mg/mL to 120 mg/mL, or from 40 mg/mL to 150 mg/mL. In terms of upper limits, the salt concentration in the precipitation solution can be less than 150 mg/mL, e.g., less than 120 mg/mL, less than 95 mg/mL, less than 75 mg/mL, less than 60 mg/mL, less than 50 mg/mL, less than 40 mg/mL, less than 30 mg/mL, less than 25 mg/mL, or less than 20 mg/mL. In terms of lower limits, the salt concentration in the precipitation solution can be greater than 15 mg/mL, e.g., greater than 20 mg/mL, greater than 25 mg/mL, greater than 30 mg/mL, greater than 40 mg/mL, greater than 50 mg/mL, greater than 60 mg/mL, greater than 75 mg/mL, greater than 95 mg/mL, or greater than 120 mg/mL.

In some embodiments, the precipitation solution comprises water and one or more water-miscible solvents. The water-miscible solvent can be, for example, DMSO. The volume percentage of the water-miscible solvent in the precipitation solution can, for example, be from 70 to 97%, e.g., from 70% to 85%, from 72% to 88%, from 75% to 91%, from 77% to 94%, or from 80% to 97%. In terms of upper limits, the percentage of the water-miscible solvent in the precipitation solution can be less than 97%, e.g., less than 94%, less than 91%, less than 88%, less than 85%, less than 82%, less than 80%, less than 77%, less than 75%, or less than 72%. In terms of upper limits, the percentage of the water-miscible solvent in the precipitation solution can be greater than 70%, e.g., greater than 72%, greater than 75%, greater than 77%, greater than 80%, greater than 82%, greater than 85%, greater than 88%, greater than 91%, or greater than 94%.

In some embodiments, the precipitation solution is added to the extraction solvent mixture subsequent to the extraction step to induce selective precipitation of the cellulose. The ratio of the volume of the precipitation solution to the volume of the extraction solvent mixture to which the precipitation solution is added can, for example, be from 0.5 to 5, e.g., from 0.5 to 2, from 0.6 to 2.5, from 0.8 to 3.2, from 1 to 4, or from 1.3 to 5. In terms of upper limits, the volume ratio of the precipitation solution to the extraction solvent mixture can be less than 5, e.g., less than 4, less than 3.2, less than 2.5, less than 2, less than 1.6, less than 1.3, less than 1, less than 0.8, or less than 0.6. In terms of lower limits, the volume ratio of the precipitation solution to the extraction solvent mixture can be greater than 0.5, e.g., greater than 0.6, greater than 0.8, greater than 1, greater than 1.3, greater than 1.6, greater than 2, greater than 2.5, greater than 3.2, or greater than 4.

The yield of cellulose precipitated from the extraction solvent mixture can, for example, be from 50% to 100%, e.g., from 50% to 80%, from 55% to 85%, from 60% to 90%, from 65% to 95%, or from 70% to 100%. In terms of lower limits, the yield of extracted cellulose can be greater than 50%, greater than 55%, greater than 60%, greater than 65%, greater than 70%, greater than 75%, greater than 80%, greater than 85%, greater than 90%, or greater than 95%.

III. ENZYMATIC HYDROLYSIS OF CELLULOSE

The provided methods can also include operations subsequent to the extraction and optional precipitation of the cellulose from the cellulosic biomass sample, in which the cellulose is converted to monosaccharides or disaccharides. Several analytical methods can be used to determine the amounts of these simpler sugars produced from the cellulose, and this determination can then be used in turn to calculate the original amount of cellulose from which they were derived. In some embodiments, the conversion of the cellulose to monosaccharides and/or disaccharides occurs through an enzymatic hydrolysis.

The enzymatic hydrolysis steps can include providing a cellulose extraction solution as described above. In some embodiments, the enzymes and enzymatic hydrolysis reactions are compatible with the components of the cellulose extraction solution, and a mixture of saccharification enzymes can be applied directly to the cellulose extraction solution. The enzymatic hydrolyses steps can include providing a precipitated cellulose pellet as described above. The pellet can be resuspended in water, buffer, or any solvent mixture compatible with the enzymes and enzymatic hydrolysis reactions as described below.

A. Conversion of Extracted Cellulose into Glucose

In some embodiments, an enzymatic hydrolysis is used to convert the cellulose extracted from a cellulosic biomass sample to glucose. The mixture of saccharification enzymes used to convert the extracted cellulose to glucose can comprise enzymes selected from the list consisting of one or more cellulases, one or more beta-glucosidases, one or more cellobiohydrolases, and combinations thereof. In some embodiments, the mixture of saccharification enzymes used to convert the extracted cellulose to cellobiose consists of enzymes selected from the group consisting of one or more cellulases, one or more beta-glucosidases, one or more cellobiohydrolases, and combinations thereof. In some embodiments, the only enzymes in the mixture of saccharification enzymes used to convert the extracted cellulose to glucose are recombinant cellulase from *Bacillus amyloliquefaciens*, recombinant beta-glucosidase from *Agrobacterium* sp., cellobiohydrolase I from *Trichoderma longibrachiatum*, and cellobiohydrolase II from a microbial source. In all cases, the saccharification enzyme mixture can include non-enzymatic components. These non-enzymatic components can include, for example, buffers, water, solvents, metals, or other cofactors.

The saccharification enzymes used to convert the extracted cellulose into glucose can include one or more cellulases. The one or more cellulases can include, for example, an endo-1,4-beta-D-glucanase. The saccharification enzymes can include, as in Examples 3 and 4 below, recombinant cellulase from *Bacillus amyloliquefaciens*. The cellulase concentration in the enzymatic hydrolysis mixture can, for example, be from 100 U/mL to 1000 U/mL, e.g., from 100 U/mL to 400 U/mL, from 125 U/mL to 500 U/mL, from 160 U/mL to 630 U/mL, from 200 U/mL to 800 U/mL, or from 250 U/mL to 1000 U/mL. In terms of upper limits, the cellulase concentration in the enzymatic hydrolysis mixture can be less than 1000 U/mL, e.g., less than 800 U/mL, less than 630 U/mL, less than 500 U/mL, less than 400 U/mL, less than 325 U/mL, less than 250 U/mL, less than 200 U/mL, less than 160 U/mL, or less than 125 U/mL. In terms of lower limits, the cellulase concentration in the enzymatic hydrolysis mixture can be greater than 100 U/mL, e.g., greater than 125 U/mL, greater than 160 U/mL, greater than 200 U/mL, greater than 250 U/mL, greater than 325 U/mL, greater than 400 U/mL, greater than 500 U/mL, greater than 630 U/mL, or greater than 800 U/mL. As used herein, one unit (U) of cellulase activity is defined as the amount of enzyme required to release one μmole of glucose per minute from 4 M carboxymethyl cellulose in 100 mM sodium phosphate buffer at pH 6 and 40° C.

The saccharification enzymes used to convert the extracted cellulose into glucose can include one or more beta-glucosidases. The saccharification enzymes can include, as in Example 3 below, recombinant beta-glucosidase from *Agrobacterium* sp. The beta-glucosidase concentration in the enzymatic hydrolysis mixture can, for example, be from 12 U/mL to 120 U/mL, e.g., from 12 U/mL to 50 U/mL, from 15 U/mL to 60 U/mL, from 20 U/mL to 75 U/mL, from 25 U/mL to 95 U/mL, or from 30 U/mL to 120 U/mL. In terms of upper limits, the beta-glucosidase concentration in the enzymatic hydrolysis mixture can be less than 120 U/mL, e.g., less than 95 U/mL, less than 75 U/mL, less than 60 U/mL, less than 50 U/mL, less than 40 U/mL, less than 30 U/mL, less than 25 U/mL, less than 20 U/mL, or less than 15 U/mL. In terms of lower limits, the beta-glucosidase concentration in the enzymatic hydrolysis mixture can be greater than 12 U/mL, e.g., greater than 15 U/mL, greater than 20 U/mL, greater than 25 U/mL, greater than 30 U/mL, greater than 40 U/mL, greater than 50 U/mL, greater than 60 U/mL, greater than 75 U/mL, or greater than 95 U/mL. As used herein, one unit (U) of beta-glucosidase activity is defined as the amount of enzyme required to release one μmole of p-nitrophenol per minute from 10 mM p-nitrophenyl-beta-D-glucopyranoside in 50 mM sodium maleate buffer at pH 6.5 and 40° C.

The saccharification enzymes used to convert the extracted cellulose into glucose can include one or more cellobiohydrolases in conjunction with β-glucosidase. The saccharification enzymes can include, for example, cellobiohydrolase I from *Trichoderma longibrachiatum*. The saccharification enzymes can include, for example, cellobiohydrolase II from a microbial source. The saccharification enzymes can include, as in Examples 3 and 4 below, both cellobiohydrolase I and cellobiohydrolase II. The cellobiohydrolase concentration in the enzymatic hydrolysis mixture can, for example, be from 2.5 U/mL to 25 U/mL, e.g., from 2.5 U/mL to 10 U/mL, from 3 U/mL to 12.5 U/mL, from 4 U/mL to 16 U/mL, from 5 U/mL to 20 U/mL, or from 6 U/mL to 25 U/mL. In terms of upper limits, the cellobiohydrolase concentration in the enzymatic hydrolysis mixture can be less than 25 U/mL, e.g., less than 20 U/mL, less than 16 U/mL, less than 12.5 U/mL, less than 10 U/mL, less than 8 U/mL, less than 6 U/mL, less than 5 U/mL, less than 4 U/mL, or less than 3 U/mL. In terms of lower limits, the cellobiohydrolase concentration in the enzymatic hydrolysis mixture can be greater than 2.5 U/mL, e.g., greater than 3 U/mL, greater than 4 U/mL, greater than 5 U/mL, greater than 6 U/mL, greater than 8 U/mL, greater than 10 U/mL, greater than 12.5 U/mL, greater than 16 U/mL, or greater than 20 U/mL. As used herein, one unit (U) of cellobiohydrolase activity is defined as the amount of enzyme required to release one μmole of glucose per minute from 10 mg/mL 1,4-beta-D-cellopentaitol in 100 mM sodium acetate buffer at pH 5.5 and 40° C.

The saccharification enzymes used to convert the extracted cellulose into glucose can be combined in a buffer having a pH selected to balance the different activities and/or stabilities of the various enzymes within the enzymatic hydrolysis mixture. In some embodiments, the buffer is a phosphate buffer. The buffer can have, for example, a pH that is from 4.5 to 8, e.g., from 4.5 to 6.6, from 4.85 to 6.95, from 5.2 to 7.3, from 5.55 to 7.65, or from 5.9 to 8. The buffer pH can be from 5.5 to 6.5, e.g., from 5.5 to 6.1, from 5.6 to 6.2, from 5.7 to 6.3, from 5.8 to 6.4, or from 5.9 to 6.5. In terms of upper limits, the pH of the enzymatic hydrolysis mixture can be less than 8, e.g., less than 7.65, less than 7.3, less than 6.95, less than 6.6, less than 6.5, less than 6.4, less than 6.3, less than 6.2, less than 6.1, less than 6.0, less than 5.9, less than 5.8, less than 5.7, less than 5.6, less than 5.2, or less than 4.85. In terms of lower limits, the pH of the enzymatic hydrolysis mixture can be greater than 4.5, e.g., greater than 4.85, greater than 5.2, greater than 5.5, greater than 5.6, greater than 5.7, greater than 5.8, greater than 5.9, greater than 6.0, greater than 6.1, greater than 6.2, greater than 6.3, greater than 6.4, greater than 6.5, greater than 6.6, greater than 6.95, greater than 7.3, or greater than 7.65.

The enzymatic hydrolysis for converting the extracted cellulose into glucose can be carried out for a reaction time that can, for example, be from 30 minutes to 240 minutes, e.g., from 30 minutes to 105 minutes, from 35 minutes to 130 minutes, from 45 minutes, to 160 minutes, from 55 minutes to 195 minutes, or from 70 minutes, to 240 minutes. In terms of upper limits, the reaction time of the enzymatic hydrolysis can be less than 240 minutes, e.g., less than 195 minutes, less than 160 minutes, less than 130 minutes, less than 105 minutes, less than 85 minutes, less than 70 minutes, less than 55 minutes, less than 45 minutes, or less than 35 minutes. In terms of lower limits, the reaction time of the enzymatic hydrolysis can be greater than 30 minutes, e.g., greater than 35 minutes, greater than 45 minutes, greater than 55 minutes, greater than 70 minutes, greater than 85 minutes, greater than 105 minutes, greater than 130 minutes, greater than 160 minutes, or greater than 195 minutes. The enzymatic hydrolysis can be carried out overnight, e.g., for up to 1440 minutes, or for greater than 1440 minutes.

The enzymatic hydrolysis for converting the extracted cellulose into glucose can be carried out at a reaction temperature that can, for example, be from 20° C. to 80° C., e.g., from 20° C. to 56° C., from 26° C. to 62° C., from 32° C. to 68° C., from 38° C. to 74° C., or from 44° C. to 80° C. In terms of upper limits, the reaction temperature for the enzymatic hydrolysis can be less than 80° C., less than 74° C., less than 68° C., less than 62° C., less than 56° C., less than 50° C., less than 44° C., less than 38° C., less than 32° C., or less than 26° C. In terms of lower limits, the reaction temperature for the enzymatic hydrolysis can be greater than 20° C., e.g., greater than 26° C., greater than 32° C., greater than 38° C., greater than 44° C., greater than 50° C., greater than 56° C., greater than 62° C., greater than 68° C., or greater than 74° C.

B. Conversion of Extracted Cellulose into Cellobiose

As an alternative to the enzymatic hydrolysis of the extracted cellulose to glucose as described above, different enzymatic reaction conditions can be used to hydrolyze the extracted cellulose to cellobiose. In some embodiments, the quantification of the resulting cellobiose can provide a more accurate reflection of the cellulose concentration in the extractant or initial cellulosic biomass sample. This is because while glucose can originate from multiple saccharides within the original sample, cellobiose can predominantly or exclusively originate from cellulose.

In some embodiments, the enzymatic reaction conditions used to generate cellobiose are identical to those that would be used to generate glucose, but without the addition of beta-glucosidase to the cocktail or mixture of saccharification enzymes. In some embodiments, the saccharification enzymes used to generate cellobiose also do not include cellulases. In some embodiments, the mixture of saccharification enzymes used to convert the extracted cellulose to cellobiose comprises enzymes selected from the list consisting of one or more cellulases, one or more cellobiohydrolases, and combinations thereof. In some embodiments, the mixture of saccharification enzymes used to convert the extracted cellulose to cellobiose consists of enzymes selected from the group consisting of one or more cellulases, one or more cellobiohydrolases, and combinations thereof. In some embodiments, the only enzymes in the mixture of saccharification enzymes used to convert the extracted cellulose to cellobiose are recombinant cellulase from *Bacillus amyloliquefaciens*, cellobiohydrolase I from *Trichoderma longibrachiatum*, and cellobiohydrolase II from a microbial source. In all cases, the saccharification enzyme mixture can include non-enzymatic components. These non-enzymatic components can include, for example, buffers, water, solvents, metals, or other cofactors.

The saccharification enzymes used to convert the extracted cellulose into cellobiose can include one or more cellulases. The saccharification enzymes can include, for example, recombinant cellulase from *Bacillus amyloliquefaciens*. The cellulase concentration in the enzymatic hydrolysis mixture can, for example, be from 100 U/mL to 1000 U/mL, e.g., from 100 U/mL to 400 U/mL, from 125 U/mL to 500 U/mL, from 160 U/mL to 630 U/mL, from 200 U/mL to 800 U/mL, or from 250 U/mL to 1000 U/mL. In terms of upper limits, the cellulase concentration in the enzymatic hydrolysis mixture can be less than 1000 U/mL, e.g., less than 800 U/mL, less than 630 U/mL, less than 500 U/mL, less than 400 U/mL, less than 325 U/mL, less than 250 U/mL, less than 200 U/mL, less than 160 U/mL, or less than 125 U/mL. In terms of lower limits, the cellulase concentration in the enzymatic hydrolysis mixture can be greater than 100 U/mL, e.g., greater than 125 U/mL, greater than 160 U/mL, greater than 200 U/mL, greater than 250 U/mL, greater than 325 U/mL, greater than 400 U/mL, greater than 500 U/mL, greater than 630 U/mL, or greater than 800 U/mL.

The saccharification enzymes used to convert the extracted cellulose into cellobiose can include one or more cellobiohydrolases. The saccharification enzymes can include, for example, cellobiohydrolase I from *Trichoderma longibrachiatum*. The saccharification enzymes can include, for example, cellobiohydrolase II from a microbial source. The saccharification enzymes can include both cellobiohydrolase I and cellobiohydrolase II. The cellobiohydrolase concentration in the enzymatic hydrolysis mixture can, for example, be from 2.5 U/mL to 25 U/mL, e.g., from 2.5 U/mL to 10 U/mL, from 3 U/mL to 12.5 U/mL, from 4 U/mL to 16 U/mL, from 5 U/mL to 20 U/mL, or from 6 U/mL to 25 U/mL. In terms of upper limits, the cellobiohydrolase concentration in the enzymatic hydrolysis mixture can be less than 25 U/mL, e.g., less than 20 U/mL, less than 16 U/mL, less than 12.5 U/mL, less than 10 U/mL, less than 8 U/mL, less than 6 U/mL, less than 5 U/mL, less than 4 U/mL, or less than 3 U/mL. In terms of lower limits, the cellobiohydrolase concentration in the enzymatic hydrolysis mixture can be greater than 2.5 U/mL, e.g., greater than 3 U/mL, greater than 4 U/mL, greater than 5 U/mL, greater than 6 U/mL, greater than 8 U/mL, greater than 10 U/mL, greater than 12.5 U/mL, greater than 16 U/mL, or greater than 20 U/mL.

The saccharification enzymes used to convert the extracted cellulose into cellobiose can be combined in a buffer having a pH selected to balance the different activities and/or stabilities of the various enzymes within the enzymatic hydrolysis mixture. In some embodiments, the buffer is a phosphate buffer. The buffer can have, for example, a pH that is from 4.5 to 8, e.g., from 4.5 to 6.6, from 4.85 to 6.95, from 5.2 to 7.3, from 5.55 to 7.65, or from 5.9 to 8. The buffer pH can be from 5.5 to 6.5, e.g., from 5.5 to 6.1, from 5.6 to 6.2, from 5.7 to 6.3, from 5.8 to 6.4, or from 5.9 to 6.5. In terms of upper limits, the pH of the enzymatic hydrolysis mixture can be less than 8, e.g., less than 7.65, less than 7.3, less than 6.95, less than 6.6, less than 6.5, less than 6.4, less than 6.3, less than 6.2, less than 6.1, less than 6.0, less than 5.9, less than 5.8, less than 5.7, less than 5.6, less than 5.2, or less than 4.85. In terms of lower limits, the pH of the enzymatic hydrolysis mixture can be greater than 4.5, e.g., greater than 4.85, greater than 5.2, greater than 5.5, greater than 5.6, greater than 5.7, greater than 5.8, greater than 5.9, greater than 6.0, greater than 6.1, greater than 6.2, greater than 6.3, greater than 6.4, greater than 6.5, greater than 6.6, greater than 6.95, greater than 7.3, or greater than 7.65.

The enzymatic hydrolysis for converting the extracted cellulose into cellobiose can be carried out for a reaction time that can, for example, be from 30 minutes to 240 minutes, e.g., from 30 minutes to 105 minutes, from 35 minutes to 130 minutes, from 45 minutes, to 160 minutes, from 55 minutes to 195 minutes, or from 70 minutes, to 240 minutes. In terms of upper limits, the reaction time of the enzymatic hydrolysis can be less than 240 minutes, e.g., less than 195 minutes, less than 160 minutes, less than 130 minutes, less than 105 minutes, less than 85 minutes, less than 70 minutes, less than 55 minutes, less than 45 minutes, or less than 35 minutes. In terms of lower limits, the reaction time of the enzymatic hydrolysis can be greater than 30 minutes, e.g., greater than 35 minutes, greater than 45 minutes, greater than 55 minutes, greater than 70 minutes, greater than 85 minutes, greater than 105 minutes, greater than 130 minutes, greater than 160 minutes, or greater than 195 minutes. The enzymatic hydrolysis can be carried out overnight, e.g., for up to 1440 minutes, or for greater than 1440 minutes.

The enzymatic hydrolysis for converting the extracted cellulose into cellobiose can be carried out at a reaction temperature that can, for example, be from 20° C. to 80° C., e.g., from 20° C. to 56° C., from 26° C. to 62° C., from 32° C. to 68° C., from 38° C. to 74° C., or from 44° C. to 80° C. In terms of upper limits, the reaction temperature for the enzymatic hydrolysis can be less than 80° C., less than 74° C., less than 68° C., less than 62° C., less than 56° C., less than 50° C., less than 44° C., less than 38° C., less than 32° C., or less than 26° C. In terms of lower limits, the reaction temperature for the enzymatic hydrolysis can be greater than 20° C., e.g., greater than 26° C., greater than 32° C., greater than 38° C., greater than 44° C., greater than 50° C., greater than 56° C., greater than 62° C., greater than 68° C., or greater than 74° C.

In some embodiments, the extracted cellulose is also subjected to an additional enzymatic step to further remove starch and/or other saccharide molecules. For example, glucoamylase can be used to remove starch oligosaccharides, and trehalase can be used to remove trehalose.

IV. ACID HYDROLYSIS OF CELLULOSE

In some embodiments, the conversion of the cellulose to monosaccharides occurs through chemical means, such as an acid hydrolysis. Because acid hydrolysis can be a less selective saccharide degradation process, it can be important for the cellulose isolation steps, either through cellulose extraction or cellulose precipitation, to supply the needed selectivity. For example, if a cellulose extraction also extracts starch and/or other non-cellulose saccharide components, then a selective precipitation operation can be used after an extraction and before an acid hydrolysis.

The acid hydrolysis steps can include providing an extracted and precipitated cellulose pellet as described above. The pellet can be resuspended in water, buffer, or any solvent mixture compatible with the acid hydrolysis reactions as described below. The acid hydrolysis further includes adding the cellulose pellet or the resuspended cellulose pellet to a pressure resistant vessel, such as for example, a pressure tube.

A strong acid is then added to the vessel. The strong acid can be, for example, 72% w/w sulfuric acid. The volume of acid added per pellet or resuspended pellet mass can, for example, be from 1.5 mL/g to 15 mL/g, e.g., from 1.5 mL/g to 6 mL/g, from 2 mL/g to 7.5 mL/g, from 2.5 mL/g to 9.5 mL/g, from 3 mL/g to 12 mL/g, or from 4 mL/g to 15 mL/g. In terms of upper limits, the volume of strong acid added per pellet mass can be less than 15 mL/g, e.g., less than 12 mL/g, less than 9.5 mL/g, less than 7.5 mL/g, less than 6 mL/g, less than 5 mL/g, less than 4 mL/g, less than 3 mL/g, less than 2.5 mL/g, or less than 2 mL/g. In terms of lower limits, the volume of strong acid added per pellet mass can be greater than 1.5 mL/g, e.g., greater than 2 mL/g, greater than 2.5 mL/g, greater than 3 mL/g, greater than 4 mL/g, greater than 5 mL/g, greater than 6 mL/g, greater than 7.5 mL/g, greater than 9.5 mL/g, or greater than 12 mL/g.

The acid hydrolysis steps can include ageing the resulting strong acid mixture for a particular time and a particular temperature. The strong acid mixture ageing time can, for example, be from 20 minutes to 180 minutes, e.g., from 20 minutes to 75 minutes, from 25 minutes to 95 minutes, from 30 minutes to 115 minutes, from 40 minutes to 145 minutes, or from 50 minutes to 180 minutes. In terms of upper limits, the ageing time can be less than 180 minutes, e.g., less than 145 minutes, less than 115 minutes, less than 95 minutes, less than 75 minutes, less than 60 minutes, less than 50 minutes, less than 40 minutes, less than 30 minutes, or less than 25 minutes. In terms of lower limits, the ageing time can be greater than 20 minutes, e.g., greater than 25 minutes, greater than 30 minutes, greater than 40 minutes, greater than 50 minutes, greater than 60 minutes, greater than 75 minutes, greater than 95 minutes, greater than 115 minutes, or greater than 115 minutes. The strong acid mixture ageing temperature can, for example, be from 20° C. to 50° C., e.g., from 20° C. to 38° C., from 23° C. to 41° C., from 26° C. to 44° C., from 29° C. to 47° C., or from 32° C. to 50° C. In terms of upper limits, the strong acid mixture ageing temperature can be less than 50° C., e.g., less than 47° C., less than 44° C., less than 41° C., less than 38° C., less than 35° C., less than 32° C., less than 29° C., less than 26° C., or less than 23° C. In terms of lower limits, the strong acid mixture ageing temperature can be greater than 20° C., e.g., greater than 23° C., greater than 26° C., greater than 29° C., greater than 32° C., greater than 35° C., greater than 38° C., greater than 41° C., greater than 44° C., or greater than 47° C.

After the strong acid mixture has been aged for the desired period of time, water can be added to the vessel to dilute the acid. The ratio of the volume of water added to the volume of strong acid that was added can, for example, be from 3 to 30, e.g., from 3 to 12, from 4 to 15, from 5 to 19, from 6 to 24, or from 8 to 30. In terms of upper limits, the ratio of the water volume to the strong acid volume can be less than 30, e.g., less than 24, less than 19, less than 15, less than 12, less than 10, less than 8, less than 6, less than 5, or less than 4. In terms of lower limits, the ratio of the water volume to the strong acid volume can be greater than 3, e.g., greater than 4, greater than 5, greater than 6, greater than 8, greater than 10, greater than 12, greater than 15, greater than 19, or greater than 24. After the acid is thus diluted, the vessel can be sealed, heated, and pressurized. For example, the vessel can be autoclaved for 1 hour in the fluid cycle of an autoclave at a temperature of 122° C. The vessel is then cooled, and the acid hydrolyzed contents within can be neutralized. In some embodiments, the neutralizing includes adding a solid base until the resulting solution has a pH that is from 6 to 9. In some embodiments, the solid base is calcium carbonate.

V. QUANTIFICATION OF CELLULOSE

The quantity of cellulose that has been extracted from a cellulosic biomass sample as described above can be determined by assaying the cellulose itself, or complexes or downstream products thereof. A variety of different assay techniques and tools can be used to measure the concentrations of the cellulose and/or downstream products in any of the mixtures or solutions described above. If it is the downstream product of cellulose that is measured rather than the cellulose itself, conversion factors can be used to calculate cellulose amounts based on the amounts of the measured compound or compounds.

A. Glucose Determination

In some embodiments, the cellulose in the original cellulosic biomass sample is quantified in part by determining the concentration of glucose in a hydrolysis of extracted cellulose. The glucose can be quantified, for example, by using a colorimetric or chromatographic assay. In some embodiments, the glucose is measured by high pressure liquid chromatography (HPLC). One method for quantifying glucose concentration with HPLC includes the use of an AMINEX® HPX-87P column, commercially available from Bio-Rad Laboratories.

After a glucose concentration has been determined, one or more mathematical transformations can be used to convert the measured value to an amount of cellulose present in the initial cellulosic biomass sample. One transformation can involve calculating the amount of glucose produced by an enzymatic or acid hydrolysis using known values of, for example, the volume of the hydrolysis solution and dilution factors of steps taken to prepare an HPLC sample from the hydrolysis solution. In some embodiments, a transformation involves multiplying the glucose monomer concentration by a correction factor to convert to a concentration of an equivalent polymer. In some embodiments, a transformation involves multiplying the glucose concentration by a correction factor to account for estimated yield losses during hydrolysis steps. In some embodiments, a transformation involves multiplying the glucose concentration by a correction factor to account for estimated yield losses during extraction steps. In some embodiments, a transformation involves multiplying the glucose concentration by a correction factor to account for estimated yield losses during precipitation steps. The estimated yield losses for any of these steps can be based on historical data. The estimated yield losses can be based on one or more controls subjected to identical steps as the sample either at a different time or in parallel with the sample.

B. Cellobiose Determination

In some embodiments, the cellulose in the original cellulosic biomass sample is quantified in part by determining the concentration of cellobiose in a hydrolysis of extracted cellulose. The cellobiose can be quantified, for example, by using a colorimetric or chromatographic assay. In some embodiments, the cellobiose is measured by HPLC. One method for quantifying cellobiose concentration with HPLC includes the use of an AMINEX® HPX-42A column, commercially available from Bio-Rad Laboratories.

In some embodiments, the cellobiose is measured by gas chromatography-mass spectrometry (GC-MS). An advantage of the use GC-MS in measuring cellobiose is that this analytical technique can be highly specific for cellobiose, e.g., GC-MS detection peaks associated with cellobiose can be readily separated from those associated with other disaccharides that may be present, such as sucrose, trehalose, maltose, and others. In certain aspects, the quantification of cellobiose formed from cellulose hydrolysis includes the derivitization of cellobiose and other saccharides by converting aldehydes to methyl oximes and alcohols to silyl ethers. The derivitization can include, for example, contacting the hydrolyzed biomass sample with methoxylamine hydrochloride and hexamethyldisilazane under conditions suitable for forming volatile derivatives of cellobiose and other saccharides.

After a cellobiose concentration has been determined, one or more mathematical transformations can be used to convert the measured value to an amount of cellulose present in the initial cellulosic biomass sample. One transformation can involve calculating the amount of cellobiose produced by an enzymatic hydrolysis using known values of, for example, the volume of the hydrolysis solution and dilution factors of steps taken to prepare an HPLC or GC-MS sample from the hydrolysis solution. In some embodiments, a transformation involves multiplying the cellobiose concentration by a correction factor to convert to a concentration of an equivalent polymer. In some embodiments, a transformation involves multiplying the cellobiose concentration by a correction factor to account for estimated yield losses during hydrolysis steps. In some embodiments, a transformation involves multiplying the cellobiose concentration by a correction factor to account for estimated yield losses during extraction steps. In some embodiments, a transformation involves multiplying the cellobiose concentration by a correction factor to account for estimated yield losses during precipitation steps. The estimated yield losses for any of these steps can be based on historical data. The estimated yield losses can be based on one or more controls subjected to identical steps as the sample either at a different time or in parallel with the sample.

C. Cellulose-Quaternary Ammonium Salt Complex Determination

In some embodiments, the cellulose in the original cellulosic biomass sample is quantified in part by determining the concentration of cellulose-quaternary ammonium salt complexes formed during extraction of the cellulose from the sample. For example, the solvent mixture used for the extraction of cellulose can include tetrabutylammonium fluoride (TBAF) and tetrabutylammonium iodide (TBAI). Without being bound by a particular theory, it is believed that the TBAF of the solvent mixture aids in the dissolution of the cellulose of the biomass sample, and the TBAI of the solvent mixture forms a triiodide ion that complexes with the cellulose and the tetrabutylammonium. Cellulose, and the cellulose-quaternary ammonium salt complexes that can be formed, have been found to have significantly different absorbance characteristics than that of starch. These different absorbance characteristics can be used in the provided methods to spectrophotometrically determine concentration measurements of cellulose complexes unaffected by the presence of any commingled starch.

For example, cellulose has a stronger absorbance than starch of light having a wavelength of 320 nm. In some embodiments, the amount of cellulose or cellulose complex within an extraction mixture is determined by measuring the absorbance of the extraction mixture at 320 nm. A standard curve and a curve-fitting function can be developed to relate various concentrations of cellulose or cellulose-quaternary ammonium complex to their resulting absorbance at 320 nm. By subsequently applying this standard curve and fitting function (i.e., transforming assay values), measurements of extraction mixture absorbance at 320 nm can be used to calculate corresponding concentrations of cellulose or cellulose-quaternary complex within the extraction mixture.

Some oligosaccharides or other impurities within the extraction mixture can also cause significant absorbance of light having a wavelength at 320 nm. In some embodiments, a chromatography system, such as an HPLC, is used to separate components of the extraction mixture from one another, while the effluent from the chromatography column is assayed for its absorbance at 320 nm.

VI. BIOMASS PRETREATMENT METHODS

Also provided are pretreatment methods useful for preparing cellulosic biomass samples for extraction of cellulose. In certain aspects, the pretreatment of the biomass prior to the cellulose extraction has been found to significantly increase the accuracy of subsequent determinations of the cellulose content of the biomass. One cause of this increased accuracy is an improvement to the accessibility of cellulose within the structure of the biomass. For example, some cellulosic materials include, in addition to cellulose, components such as lignin, arabinoxylan or other hemicelluloses, starch, or protein. These additional materials can be present in the form of dense networks or complexes that limit the access of any interior cellulose to chemicals or enzymes used to extract, dissolve, or hydrolyze the biomass cellulose. In such cases, pretreatment conditions and process can be used to remove occluding material and/or to introduce spaces, voids, or channels through which the cellulose can be more readily accessed.

Another source of increased cellulose quantification accuracy resulting from biomass pretreatment is that some biomass components in addition to cellulose can themselves generate simple sugars, such as glucose, during chemical or enzymatic cellulose hydrolysis operations. Because some techniques for quantifying cellulose involve directly or indirectly measuring the amount of such simple sugars formed from cellulose as a starting material, the presence of simple sugars originating from other starting materials can lead to an over-estimation of the amount of cellulose originally present in the biomass. In such cases, the ability of one or more pretreatment steps to physically or chemically remove these other starting materials can increase the accuracy of calculations relating product simple sugar (e.g., glucose) measurements with substrate cellulose concentrations.

A further reason that biomass pretreatment steps can have a beneficial impact on cellulose isolation and assessment is that some biomass components can have an inhibitory effect on processes used to convert the biomass cellulose. For example, the common hemicellulose material, arabinoxylan, has been shown to inhibit the activity of cellulase enzymes. In such cases, the degradation or removal of arabinoxylan or other inhibitors through biomass pretreatment can improve the rate and extent of cellulose conversion in hydrolyses carried out after the pretreatment.

Any of the following pretreatment operations can be used individually or in combination to pretreat the cellulosic biomass sample. When combined, the pretreatment operations can be used sequentially in any order, or simultaneously.

A. Biomass Swelling

The cellulose isolation method can optionally include, prior to the cellulose extraction as described above, one or more pretreatment steps to alter the physical structure of the biomass. The pretreatment steps can, for example, act to swell the biomass. Without being bound by a particular theory, it is believed that biomass swelling pretreatment processes can break bonds (e.g., ester bonds) between arabinoxylan and ferulic acid moieties of lignin, and between acetyl groups, within the biomass. As discussed above, in this way the swelling pretreatment can improve the access to cellulose within the interior of a biomass sample, and can disrupt some functional groups that can inhibit the enzymatic hydrolysis of cellulose.

In some embodiments, the cellulose isolation method includes pretreating the cellulosic biomass sample with a biomass swelling solution comprising one or more metal hydroxides. The swelling pretreatment operation can include contacting the biomass sample with a swelling solution for a swelling pretreatment time at a selling pretreatment temperature. In certain aspects, the swelling solution is an aqueous solution including one or more metal hydroxides. The swelling solution can include, for example, sodium hydroxide, potassium hydroxide, or a combination thereof. In some embodiments, after contacting the biomass sample with a basic metal hydroxide solution for a desired swelling pretreatment time, the mixture is at least partially neutralized with the addition of an acidic solution. In some embodiments, the acidic solution is aqueous acetic acid at a concentration of 3% to 30% weight/volume.

The concentration (weight/volume) of metal hydroxide in the swelling solution can, for example, be between 3% and 30%, e.g., between 3% and 12%, between 3.8% and 15%, between 4.8% and 19%, between 6% and 24%, or between 7.5% and 30%. In terms of upper limits, the metal hydroxide concentration in the swelling solution can be less than 30%, e.g., less than 24%, less than 19%, less than 15%, less than 12%, less than 9.5%, less than 7.5%, less than 6%, less than 4.8%, or less than 3.8%. In terms of lower limits, the metal hydroxide concentration in the swelling solution can be greater than 3%, e.g., greater than 3.8%, greater than 4.8%, greater than 6%, greater than 7.5%, greater than 9.5%, greater than 12%, greater than 15%, greater than 19%, or greater than 24%. Higher concentrations, e.g., greater than 30%, and lower concentrations, e.g., less than 3%, are also contemplated.

The swelling pretreatment temperature can, for example, be between 15° C. and 37° C., e.g., between 15° C. and 28.2° C., between 17.2° C. and 30.4° C., between 19.4° C. and 32.6° C., between 21.6° C. and 34.8° C., or between 23.8° C. and 37° C. In terms of upper limits, the swelling pretreatment temperature can be less than 37° C., e.g., less than 34.8° C., less than 32.6° C., less than 30.4° C., less than 28.2° C., less than 26° C., less than 23.8° C., less than 21.6° C., less than 19.4° C., or less than 17.2° C. In terms of lower limits, the swelling pretreatment temperature can be greater than 15° C., e.g., greater than 17.2° C., greater than 19.4° C., greater than 21.6° C., greater than 23.8° C., greater than 26° C., greater than 28.2° C., greater than 30.4° C., greater than 32.6° C., or greater than 34.8° C. Higher temperatures, e.g., greater than 37° C., and lower temperatures, e.g., less than 15° C., are also contemplated.

The swelling pretreatment time can, for example, be from 18 minutes to 180 minutes, e.g., from 18 minutes to 72 minutes, from 23 minutes to 90 minutes, from 29 minutes to 114 minutes, from 36 minutes to 143 minutes, or from 45 minutes to 180 minutes. In terms of upper limits, the swelling pretreatment time can be less than 180 minutes, e.g., less than 143 minutes, less than 143 minutes, less than 114 minutes, less than 90 minutes, less than 72 minutes, less than 57 minutes, less than 45 minutes, less than 36 minutes, less than 29 minutes, or less than 23 minutes. In terms of lower limits, the swelling pretreatment time can be greater than 18 minutes, e.g., greater than 23 minutes, greater than 29 minutes, greater than 36 minutes, greater than 45 minutes, greater than 57 minutes, greater than 72 minutes, greater than 90 minutes, greater than 114 minutes, or greater than 143 minutes. Longer times, e.g., greater than 180 minutes, and shorter times, e.g., less than 18 minutes, are also contemplated. In some embodiments, the cellulose isolation method includes more than one swelling pretreatment step, each independently having a swelling pretreatment time as described above.

B. Enzymatic Hydrolysis

The cellulose isolation method can optionally include, prior to the cellulose extraction as described above, one or more pretreatment steps to degrade (e.g., hydrolyze) one or more other components of the biomass. The pretreatment steps can, for example, act to hydrolyze one or more biomass hemicellulose components, such as arabinoxylan. As discussed above, arabinoxylan can inhibit the activity of cellulases used to hydrolyze the biomass cellulose, and the digestibility of cellulose has been shown in certain aspects to correlate with the removal of arabinoxylan.

In some embodiments, the cellulose isolation method includes pretreating the cellulosic biomass with an enzyme solution comprising one or more xylanases. The xylanase pretreatment operation can include contacting the biomass sample with a xylanase solution for a xylanase pretreatment time at a xylanase pretreatment temperature. The one or more xylanases of the xylanase solution can include, for example, an endo-1,4-beta-xylanase from *Neocallimastix patriciarum*, a beta-xylosidase from *Bacillus pumilus*, an arabinofuranosidase from *Bacteroides ovatus*, or a combination thereof. In some embodiments, a mixture including the biomass sample is contacted with an equal volume of the xylanase solution.

The endo-1,4-beta-xylanase concentration in the xylanase solution can, for example, be from 50 U/mL to 500 U/mL, e.g., from 50 U/mL to 200 U/mL, from 60 U/mL to 250 U/mL, from 80 U/mL to 315 U/mL, from 100 U/mL to 400 U/mL, or from 125 U/mL to 500 U/mL. In terms of upper limits, the endo-1,4-beta-xylanase concentration in the xylanase solution can be less than 500 U/mL, e.g., less than 400 U/mL, less than 315 U/mL, less than 250 U/mL, less than 200 U/mL, less than 160 U/mL, less than 125 U/mL, less than 100 U/mL, less than 80 U/mL, or less than 60 U/mL. In terms of lower limits, the endo-1,4-beta-xylanase concentration in the xylanase solution can be greater than 50 U/mL, e.g., greater than 60 U/mL, greater than 80 U/mL, greater than 100 U/mL, greater than 125 U/mL, greater than 160 U/mL, greater than 200 U/mL, greater than 250 U/mL, greater than 315 U/mL, or greater than 400 U/mL. Higher concentrations, e.g., greater than 500 U/mL, and lower concentrations, e.g., less than 50 U/mL, are also contemplated. As used herein, one unit (U) of endo-1,4-beta-xylanase activity is defined as the amount of enzyme required to release one μmole of xylose reducing-sugar equivalents per minute from 5 mg/mL wheat arabinoxylan in 100 mM sodium phosphate buffer at pH 6.0.

The beta-xylosidase concentration in the xylanase solution can, for example, be from 3 U/mL to 30 U/mL, e.g., from 3 U/mL to 12 U/mL, from 3.8 U/mL to 15 U/mL, from 4.8 U/mL to 19 U/mL, from 6 U/mL to 24 U/mL, or from 7.5 U/mL to 30 U/mL. In terms of upper limits, the beta-xylosidase concentration is the xylanase solution can be less than 30 U/mL, e.g., less than 24 U/mL, less than 19 U/mL, less than 15 U/mL, less than 12 U/mL, less than 9.5 U/mL, less than 7.5 U/mL, less than 6 U/mL, less than 4.8 U/mL, or less than 3.8 U/mL. In terms of lower limits, the beta-xylosidase concentration is the xylanase solution can be greater than 3 U/mL, e.g., greater than 3.8 U/mL, greater than 4.8 U/mL, greater than 6 U/mL, greater than 7.5 U/mL, greater than 9.5 U/mL, greater than 15 U/mL, greater than 19 U/mL, or greater than 24 U/mL. Higher concentrations, e.g., greater than 30 U/mL, and lower concentrations, e.g., less than 3 U/mL, are also contemplated. As used herein, one unit (U) of beta-xylosidase activity is defined as the amount of enzyme required to release one μmole of p-nitrophenol per minute from 5 mM p-nitrophenyl-beta-D-xylopyranoside in 50 mM potassium phosphate buffer at pH 7.5 and 35° C.

The arabinofuranosidase concentration in the xylanase solution can, for example, be from 3 U/mL to 30 U/mL, e.g., from 3 U/mL to 12 U/mL, from 3.8 U/mL to 15 U/mL, from 4.8 U/mL to 19 U/mL, from 6 U/mL to 24 U/mL, or from 7.5 U/mL to 30 U/mL. In terms of upper limits, the arabinofuranosidase concentration is the xylanase solution can be less than 30 U/mL, e.g., less than 24 U/mL, less than 19 U/mL, less than 15 U/mL, less than 12 U/mL, less than 9.5 U/mL, less than 7.5 U/mL, less than 6 U/mL, less than 4.8 U/mL, or less than 3.8 U/mL. In terms of lower limits, the arabinofuranosidase concentration is the xylanase solution can be greater than 3 U/mL, e.g., greater than 3.8 U/mL, greater than 4.8 U/mL, greater than 6 U/mL, greater than 7.5 U/mL, greater than 9.5 U/mL, greater than 15 U/mL, greater than 19 U/mL, or greater than 24 U/mL. Higher concentrations, e.g., greater than 30 U/mL, and lower concentrations, e.g., less than 3 U/mL, are also contemplated. As used herein, one unit (U) of arabinofuranosidase activity is defined as the amount of enzyme required to release one μmole of arabinose per minute from 10 mg/mL wheat arabinoxylan in 100 mM sodium phosphate buffer at pH 7.5 and 40° C.

The xylanase pretreatment time can, for example, be from 1 hour to 50 hours, e.g., from 1 hour to 10 hours, from 1.5 hours to 15 hours, from 2.2 hours to 23 hours, from 3.2 hours to 34 hours, or from 4.8 hours to 50 hours. In terms of upper limits, the xylanase pretreatment time can be less than 50 hours, e.g., less than 34 hours, less than 23 hours, less than 15 hours, less than 10 hours, less than 7.1 hours, less than 4.8 hours, less than 3.2 hours, less than 2.2 hours, or less than 1.5 hours. In terms of lower limits, the xylanase pretreatment time can be greater than 1 hour, e.g., greater than 1.5 hours, greater than 2.2 hours, greater than 3.2 hours, greater than 4.5 hours, greater than 7.1 hours, greater than 10 hours, greater than 15 hours, greater than 23 hours, or greater than 34 hours. Longer times, e.g., greater than 50 hours, and shorter times, e.g., less than 1 hour, are also contemplated. In some embodiments, the cellulose isolation method includes more than one xylanase pretreatment step, each independently having a xylanase pretreatment time as described above.

The xylanase pretreatment temperature can, for example, be from 30° C. to 50° C., e.g., from 30° C. to 42° C., from 32° C. to 44° C., from 34° C. to 46° C., from 36° C. to 48° C., or from 38° C. to 50° C. In terms of upper limits, the xylanase pretreatment temperature can be less than 50° C., e.g., less than 48° C., less than 46° C., less than 44° C., less than 42° C., less than 40° C., less than 38° C., less than 36° C., less than 34° C., or less than 32° C. In terms of lower limits, the xylanase pretreatment temperature can be greater than 30° C., e.g., greater than 32° C., greater than 34° C., greater than 36° C., greater than 38° C., greater than 40° C., greater than 42° C., greater than 44° C., greater than 46° C., or greater than 48° C. Higher temperatures, e.g., greater than 50° C., and lower temperatures, e.g., less than 30° C., are also contemplated.

C. Nitren Extraction

The cellulose isolation method can optionally include, prior to the cellulose extraction as described above, one or more pretreatment steps to remove (e.g., extract) one or more other components of the biomass. The pretreatment steps can, for example, act to extract one or more biomass hemicellulose components, such as arabinoxylan. As discussed above, arabinoxylan can inhibit the activity of cellulases used to hydrolyze the biomass cellulose, and the digestibility of cellulose has been shown in certain aspects to correlate with the removal of arabinoxylan.

In some embodiments, the cellulose isolation method includes pretreating the cellulosic biomass with an extraction solution comprising a transition metal amine complex. The transition metal amine complex can be, for example, nitren or a copper complex such as cupren. The nitren pretreatment operation can include contacting the biomass sample with a nitren solution for a nitren pretreatment time at a nitren pretreatment temperature. Nitren has been found to be an effective extractant for the removal of hemicelluloses such as arabinoxylan from cellulosic biomass. In addition, the use of nitren to extract hemicellulose does not result in degradation of the extracted hemicellulose. This stability of the hemicellulose during the extraction allows the hemicellulose, once removed from the biomass, to be further quantified or isolated in additional analytical or separation processes.

The nitren pretreatment temperature can, for example, be between 15° C. and 37° C., e.g., between 15° C. and 28.2° C., between 17.2° C. and 30.4° C., between 19.4° C. and 32.6° C., between 21.6° C. and 34.8° C., or between 23.8° C. and 37° C. In terms of upper limits, the nitren pretreatment temperature can be less than 37° C., e.g., less than 34.8° C., less than 32.6° C., less than 30.4° C., less than 28.2° C., less than 26° C., less than 23.8° C., less than 21.6° C., less than 19.4° C., or less than 17.2° C. In terms of lower limits, the nitren pretreatment temperature can be greater than 15° C., e.g., greater than 17.2° C., greater than 19.4° C., greater than 21.6° C., greater than 23.8° C., greater than 26° C., greater than 28.2° C., greater than 30.4° C., greater than 32.6° C., or greater than 34.8° C. Higher temperatures, e.g., greater than 37° C., and lower temperatures, e.g., less than 15° C., are also contemplated.

The nitren pretreatment time can, for example, be from 18 minutes to 180 minutes, e.g., from 18 minutes to 72 minutes, from 23 minutes to 90 minutes, from 29 minutes to 114 minutes, from 36 minutes to 143 minutes, or from 45 minutes to 180 minutes. In terms of upper limits, the nitren pretreatment time can be less than 180 minutes, e.g., less than 143 minutes, less than 143 minutes, less than 114 minutes, less than 90 minutes, less than 72 minutes, less than 57 minutes, less than 45 minutes, less than 36 minutes, less than 29 minutes, or less than 23 minutes. In terms of lower limits, the nitren pretreatment time can be greater than 18 minutes, e.g., greater than 23 minutes, greater than 29 minutes, greater than 36 minutes, greater than 45 minutes, greater than 57 minutes, greater than 72 minutes, greater than 90 minutes, greater than 114 minutes, or greater than 143 minutes. Longer times, e.g., greater than 180 minutes, and shorter times, e.g., less than 18 minutes, are also contemplated. In some embodiments, the cellulose isolation method includes more than one nitren pretreatment step, each independently having a nitren pretreatment time as described above.

D. Peracetic Acid Treatment

The cellulose isolation method can optionally include, prior to the cellulose extraction as described above, one or more pretreatment steps to remove (e.g., degrade) one or more other components of the biomass. The pretreatment steps can, for example, act to degrade one or more biomass lignin or hemicellulose components. As discussed above, lignin and hemicellulose can occlude the cellulose within the biomass, limiting the accessibility of the cellulose to chemicals or enzymes used for its extraction, dissolving, or hydrolysis.

In some embodiments, the cellulose isolation method includes pretreating the cellulosic biomass with a solution comprising peracetic acid. The peracetic acid pretreatment operation can include contacting the biomass sample with a peracetic acid solution for a peracetic acid pretreatment time at a peracetic acid pretreatment temperature. Peracetic acid has been shown to be effective for degrading lignin and arabinoxylan, the predominant hemicellulose component in corn. In addition, the use of peracetic acid to degrade lignin and hemicellulose does not result in degradation of the cellulose of the biomass. This stability of the cellulose during the extraction allows the cellulose, after removal of some or all of the lignin and hemicellulose, to be further quantified or isolated in additional analytical or separation processes.

Upon contacting the biomass sample with the peracetic acid solution, the concentration (weight/volume) of peracetic acid in the combined mixture can, for example, be from 3% to 33%, e.g., from 3% to 21%, from 6% to 24%, from 9% to 27%, from 12% to 30%, or from 15% to 33%. In terms of upper limits, the peracetic acid concentration in the combined mixture can be less than 33%, e.g., less than 30%, less than 27%, less than 24%, less than 21%, less than 18%, less than 15%, less than 12%, less than 9%, or less than 6%. In terms of lower limits, the peracetic acid concentration in the combined mixture can be greater than 3%, e.g., greater than 6%, greater than 9%, greater than 12%, greater than 15%, greater than 18%, greater than 21%, greater than 24%, greater than 27%, or greater than 30%. Higher concentrations, e.g., greater than 33%, and lower concentrations, e.g., less than 3%, are also contemplated.

The peracetic acid pretreatment temperature can, for example, be between 0° C. and 100° C., e.g., between 0° C. and 60° C., between 10° C. and 70° C., between 20° C. and 80° C., between 30° C. and 90° C., or between 40° C. and 100° C. In terms of upper limits, the peracetic acid pretreatment temperature can be less than 100° C., e.g., less than 90° C., less than 80° C., less than 70° C., less than 60° C., less than 50° C., less than 40° C., less than 30° C., less than 20° C., or less than 10° C. In terms of lower limits, the peracetic acid pretreatment temperature can be greater than 0° C., e.g., greater than 10° C., greater than 20° C., greater than 30° C., greater than 40° C., greater than 50° C., greater than 60° C., greater than 70° C., greater than 80° C., or greater than 90° C. Lower temperatures, e.g., less than 0° C., are also contemplated.

The peracetic acid pretreatment time can, for example, be from 18 minutes to 180 minutes, e.g., from 18 minutes to 72 minutes, from 23 minutes to 90 minutes, from 29 minutes to 114 minutes, from 36 minutes to 143 minutes, or from 45 minutes to 180 minutes. In terms of upper limits, the peracetic acid pretreatment time can be less than 180 minutes, e.g., less than 143 minutes, less than 143 minutes, less than 114 minutes, less than 90 minutes, less than 72 minutes, less than 57 minutes, less than 45 minutes, less than 36 minutes, less than 29 minutes, or less than 23 minutes. In terms of lower limits, the peracetic acid pretreatment time can be greater than 18 minutes, e.g., greater than 23 minutes, greater than 29 minutes, greater than 36 minutes, greater than 45 minutes, greater than 57 minutes, greater than 72 minutes, greater than 90 minutes, greater than 114 minutes, or greater than 143 minutes. Longer times, e.g., greater than 180 minutes, and shorter times, e.g., less than 18 minutes, are also contemplated. In some embodiments, the cellulose isolation method includes more than one peracetic acid pretreatment step, each independently having a peracetic acid pretreatment time as described above.

E. Ethanol Precipitation

The cellulose isolation method can optionally include, prior to the cellulose extraction as describe above, one or more pretreatment steps to remove (e.g., separate) one or more other components of the biomass. The pretreatment steps can, for example, act to solubilize one or more biomass lignin or simple sugar components. As discussed above, lignin can occlude the cellulose within the biomass, and simple sugars such as glucose can confound subsequent cellulose quantification steps.

In some embodiments, the cellulose isolation method include pretreating the cellulosic biomass with a solution comprising ethanol. Ethanol has been shown to be effective for dissolving, for example, glucose and lignin fragments while keeping cellulose in a solid precipitated form. In certain aspects, ethanol precipitation operations can separate approximately 90% of biomass lignin from cellulose.

Upon contacting a biomass sample mixture with ethanol, the volume ratio of the ethanol to the biomass sample mixture can, for example, be from 5 to 50, e.g., from 5 to 20, from 6.3 to 25, from 7.9 to 32, from 10 to 40, or from 12.6 to 50. In terms of upper limits, the ratio of the ethanol volume to the biomass sample mixture volume can be less than 50, e.g., less than 39.7, less than 31.5, less than 25, less than 19.9, less than 15.8, less than 12.6, less than 10, less than 7.9, or less than 6.3. In terms of lower limits, the ratio of the ethanol volume to the biomass sample mixture volume can be greater than 5, e.g., greater than 6.3, greater than 7.9, greater than 10, greater than 12.6, greater than 15.8, greater than 19.9, greater than 25, greater than 31.5, or greater than 39.7. Higher ratios, e.g., greater than 50, and lower ratios, e.g., less than 5, are also contemplated.

VII. EXAMPLES

The present invention will be better understood in view of the following non-limiting examples.

Example 1. Procedure for Biomass Sample Pretreatment

The following is an exemplary method for pretreating a cellulosic biomass sample. Any of the operations or materials of the exemplary method can be altered as described above to provide another embodiment.

A biomass sample having a mass of 100 mg is added to a polypropylene tube and combined with 0.5 mL of a 10% potassium hydroxide solution. The mixture is aged for 1 hour at room temperature, and then neutralized with the addition of 0.5 mL of a 10% acetic acid solution. Next, 1 mL of a xylanase enzyme solution is added to the neutralized sample, and the resulting hydrolysis reaction is aged for 3 hours at 40° C. with stirring. The xylanase enzyme solution is previously prepared by combining 2.8 mL each of 110 U/mL *B. pumilis* xylosidase, 100 U/mL *B. ovatus* B25 arabinofuranosidase, and 1600 U/mL *N. patriciarum* xylanase, with 19.6 mL of a 50 mM pH 7.0 MOPS buffer. The sample is then combined with 32 mL ethanol, aged on ice for 1 hour, and centrifuged for 15 minutes at 10,000 rpm. The resulting supernatant is decanted and discarded.

The pellet from the centrifugation is resuspended in 0.5 mL of 10% potassium hydroxide, aged for 1 hour at room temperature, and neutralized with 0.5 mL of 10% acetic acid. Another 1 mL of the xylanase enzyme solution is added, and the resulting mixture is aged overnight at 40° C. with stirring. The mixture is then combined with 32 mL of ethanol, aged on ice for 1 hour, and again centrifuged for 15 minutes at 10,000 rpm. The resulting supernatant is decanted and discarded, and the pellet is subjected to a cellulose extraction procedure such as that of Example 2.

Example 2. Procedure for Cellulose Extraction

The following is an exemplary method for extracting cellulose from a cellulosic biomass sample. Any of the operations or materials of the exemplary method can be altered as described above to provide another embodiment.

One gram of a cellulosic biomass sample in the form of a liquefied corn slurry is dispensed into a polypropylene tube, frozen at −80° C., and lyophilized. A solvent mixture is prepared by dissolving TBAF and TBAOH into DMSO at concentrations of 100 mg/mL TBAF and 16 mg/mL TBAOH. The lyophilized sample is combined with 5 mL of the solvent mixture in the sample tube, which is then aged with stirring for 30-120 minutes at 50° C. The resulting extraction solution is centrifuged for 5 minutes at 4000 rpm. The supernatant is removed, and the pellet is resuspended in an additional 5 mL of the solvent mixture. The tube is again aged with stirring for 30 minutes at 50° C., and this second extraction solution is also centrifuged for 5 minutes at 4000 rpm. The second supernatant is combined with the first supernatant to produce an extracted cellulose solution.

Example 3. Procedure for Cellulose Selective Precipitation

The following is an exemplary method for selectively precipitating cellulose from a solution, e.g., the cellulose extraction solution of Example 1. Any of the operations or materials of the exemplary method can be altered as described above to provide another embodiment.

An extracted cellulose solution is prepared, for example, as described in Example 2. A precipitation solution is prepared by dissolving sodium perchlorate in a 90% DMSO/10% water mixture at a concentration of 50 mg/mL. The precipitation solution is added to the extracted cellulose solution at a ratio of 1:1, and the resulting combined solution is mixed and centrifuged. The pellet is rinsed with acetone, suspended in water, and lyophilized. The lyophilized pellet can be resuspended in water, the solvent mixture of Example 2, or any other medium suitable for cellulose determination procedures such as those of Examples 4-6.

Example 4. Procedure for Cellulose Determination Through Enzymatic Hydrolysis to Glucose The following is an exemplary method for determining an amount of cellulose in a sample by enzymatically hydrolyzing the cellulose to glucose. Any of the operations or materials of the exemplary method can be altered as described above to provide another embodiment.

An extracted and optionally precipitated cellulose solution is prepared, for example, as described in Examples 2 or 3. To a microcentrifuge tube is added 200 μL of 1400 U/mL recombinant cellulase from *Bacillus amyloliquefaciens*, 100 μL of 400 U/mL recombinant beta-glucosidase from *Agrobacterium* sp., 100 μL of cellobiohydrolase I from *Trichoderma longibrachiatum*, 100 μL of 80 U/mL cellobiohydrolase II from a microbial source, 100 μL of a pH 6 phosphate buffer, and 300 μL of water. To this mixture of saccharification enzymes, 100 μL of the extracted cellulose solution is added. The resulting enzymatic hydrolysis mixture is then aged for 4 hours at 40° C. with mixing, and then microfuged for 5 minutes. The supernatant is removed, and the pellet is resuspended in 100 µL of acetone and dried under nitrogen. The pellet is then resuspended in a mixture of 200 µL of 1400 U/mL recombinant cellulase from *Bacillus amyloliquefaciens,* 100 µL of 400 U/mL recombinant beta-glucosidase from *Agrobacterium* sp., 100 µL of cellobiohydrolase I from *Trichoderma longibrachiatum,* 100 µL of 80 U/mL cellobiohydrolase II from a microbial source, 100 µL of a pH 6 phosphate buffer, and 300 µL of water. The tube is aged overnight at 40° C. with mixing, and this second enzymatic hydrolysis mixture is also microfuged for 5 minutes. The second supernatant is combined with the first supernatant, and the combined supernatant is filtered into an HPLC vial. The glucose concentration in the combined supernatant is then measured via HPLC using a BioRad AMINEX® HPX-87P column.

Example 5. Procedure for Cellulose Determination Through Enzymatic Hydrolysis to Cellobiose The following is an exemplary method for determining an amount of cellulose in a sample by enzymatically hydrolyzing the cellulose to cellobiose. Any of the operations or materials of the exemplary method can be altered as described above to provide another embodiment.

An extracted cellulose solution is prepared, for example, as described in Examples 2 or 3. To a microcentrifuge tube is added 200 µL of 1400 U/mL recombinant cellulase from *Bacillus amyloliquefaciens,* 100 µL of 80 U/mL cellobiohydrolase II from a microbial source, 100 µL of a pH 6 phosphate buffer, and 400 µL of water. To this mixture of saccharification enzymes, 100 µL of the extracted cellulose solution is added. The resulting enzymatic hydrolysis mixture is then aged for 4 hours at 40° C. with mixing, and then microfuged for 5 minutes. The supernatant is removed, and the pellet is resuspended in 100 µL of acetone and dried under nitrogen. The pellet is then resuspended in a mixture of 200 µL of 1400 U/mL recombinant cellulase from *Bacillus amyloliquefaciens,* 100 µL of cellobiohydrolase I from *Trichoderma longibrachiatum,* 100 µL of 80 U/mL cellobiohydrolase II from a microbial source, 100 µL of a pH 6 phosphate buffer, and 500 µL of water. The tube is aged overnight at 40° C. with mixing, and this second enzymatic hydrolysis mixture is also microfuged for 5 minutes. The second supernatant is combined with the first supernatant, and to the combined supernatant is added 450 µL of glucoamylase. The combined supernatant is then aged for 60 minutes at 50° C. with stirring, and filtered into an HPLC vial. The cellobiose concentration in the combined supernatant is then measured via HPLC using a BioRad AMINEX® HPX-42A column.

Alternatively, the cellobiose concentration in the combined supernatant is measured by converting the cellobiose and other supernatant contents to volatile derivatives and analyzing by GC-MS. The combined supernatant is combined with 1-2 mL acetonitrile and dried under nitrogen at 70° C. Next, 0.5 mL of methoxylamine hydrochloride is added to the dried sample, and the mixture is aged for 30 minutes at 75° C. After this time, 0.1 mL trifluoroacetic acid and 0.9 mL hexamethyldisilazane is added, and the mixture is aged for 1 hour at 100° C. The mixture is filtered into a GC-MS vial, and the cellobiose concentration is measured via GC-MS using an Agilent HP5-MS capillary GC column.

Example 6. Procedure for Cellulose Determination Through Acid Hydrolysis to Glucose The following is an exemplary method for determining an amount of cellulose in a sample by using acid hydrolysis to convert the cellulose to glucose. Any of the operations or materials of the exemplary method can be altered as described above to provide another embodiment.

A precipitated extracted cellulose pellet is prepared, for example, as described in Examples 2 and 3. To a pressure tube is added enough of the pellet to correspond with 2 g of initial cellulosic biomass sample, as well as 9 mL of 72% sulfuric acid. The composition is manually stirred with a TEFLON® stir rod to disperse any solids, and the pressure tube is aged in a 30° C. water bath, stirring again every 10 minutes. After 1 hour, 84 mL of water are added to the pressure tube, which is then autoclaved for 1 hour in a fluid cycle at 122° C. Once the pressure tube has cooled, 10 mL of the resulting hydrolysis liquid therein is added to 1.6 g of calcium carbonate in a 50-mL beaker. Additional calcium carbonate is added to bring the hydrolysis liquid pH within the range from 6 to 9. The neutralized hydrolysis liquid is then filtered into an HPLC vial, and its glucose concentration is measured via HPLC using a BioRad AMINEX® HPX-87P column.

Example 7. Effect of TBAOH on Cellulose Extraction Yield

The effect of TBAOH on cellulose extractions similar to those using the procedure of Example 1 was tested by performing extractions in the absence of TBAOH. A portion of a cellulosic biomass sample was extracted with a solvent mixture of TBAF in DMSO, wherein the solvent mixture did not include TBAOH. After a 2-hour extraction, the extracted cellulose was converted to glucose through enzymatic hydrolysis as described in Example 4. The resulting glucose concentration, plotted as the left column in the graph of FIG. 1, was determined by HPLC as in Example 4, and was found to be low. This low glucose concentration indicated that the extraction yield of cellulose was also low. To verify that the low cellulose extraction yield was not the result of an inadequate extraction time, another portion of the cellulosic biomass sample was extracted as before, but with an extraction time of 3 hours. The resulting glucose concentration, plotted in the middle column in the graph of FIG. 1, was not significantly changed from that seen with the 2-hour extraction.

A third extraction was then carried out using another portion of the cellulosic biomass sample. For this third extraction, 16 mg/mL TBAOH was added to the solvent mixture prior to contacting the sample with the solvent mixture. After extracting the cellulose from the sample and converting the extracted cellulose to glucose, the resulting glucose concentration, as shown in the right column of the graph of FIG. 1, was found to be more than 10-fold higher than that previously observed for extractions that did not include TBAOH. This finding confirmed the benefit of including an organic base such as TBAOH in the solvent mixture used to extract cellulose from a cellulosic biomass sample.

Example 8. Effect of Extraction Time on Cellulose Extraction Yield

Figure 2:
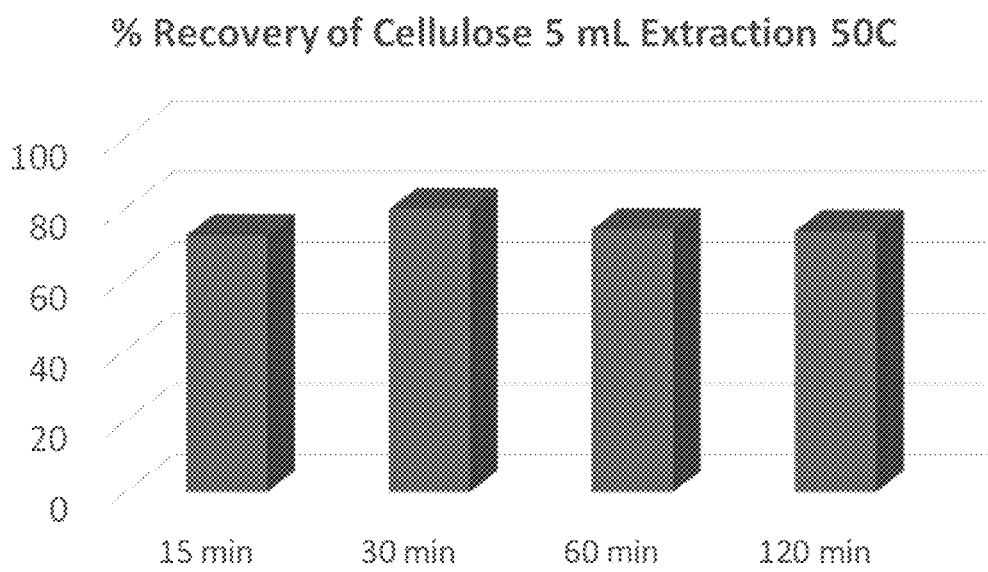
FIG. 2 is a graph of cellulose recoveries from extractions using various extraction times.

The effect of extraction time on cellulose extractions similar to those using the procedure of Example 2 was tested by performing extractions for various lengths of time. Extractions were carried out in which a sample in contact with the solvent mixture was aged at 50° C. with stirring for 15 minutes, 30 minutes, 60 minutes, or 120 minutes. The results presented in FIG. 2 show that there was minimal effect of extraction time on observed cellulose extraction yield. These findings indicate that extraction times can be at least as short as 15 minutes, and at least as long as 120 minutes, without causing an undesired decrease in cellulose extraction yields. The results also indicate that a single extraction of cellulose produces an approximately 70% yield. Therefore, because a second extraction can be expected to also have an approximately 70% yield, two sequential cellulose extractions as described in Example 2 can be expected to produce a combined cellulose extraction yield of approximately 90%.

Example 9. Effect of Extraction Volume on Cellulose Extraction Yield

Figure 3:
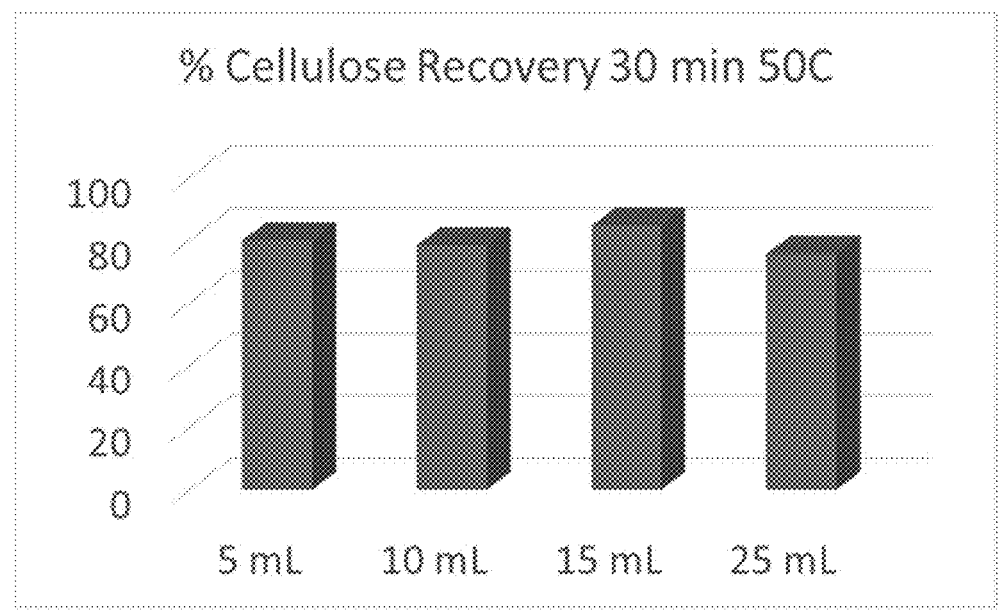
FIG. 3 is a graph of cellulose recoveries from extractions using various solvent mixture volumes.

The effect of extraction volume on cellulose extractions similar to those using the procedure of Example 2 was tested by performing extractions with various volumes of the solvent mixture. Extractions were carried out in which a sample was contacted with the solvent mixture at a ratio of solvent mixture volume per gram of sample of 5 mL/g, 10 mL/g, 15 mL/g, and 25 mL/g. The results presented in FIG. 3 show that there was minimal effect of solvent mixture volume on observed cellulose extraction yield. These findings indicate that solvent mixture volumes can be at least as low as 5 mL per gram of initial cellulosic biomass sample, and at least as high as 25 mL per gram of initial cellulosic biomass sample, without causing an undesired decrease in cellulose extraction yields.

Example 10. Hydrolysis of Cellulose to Glucose

Figure 4:
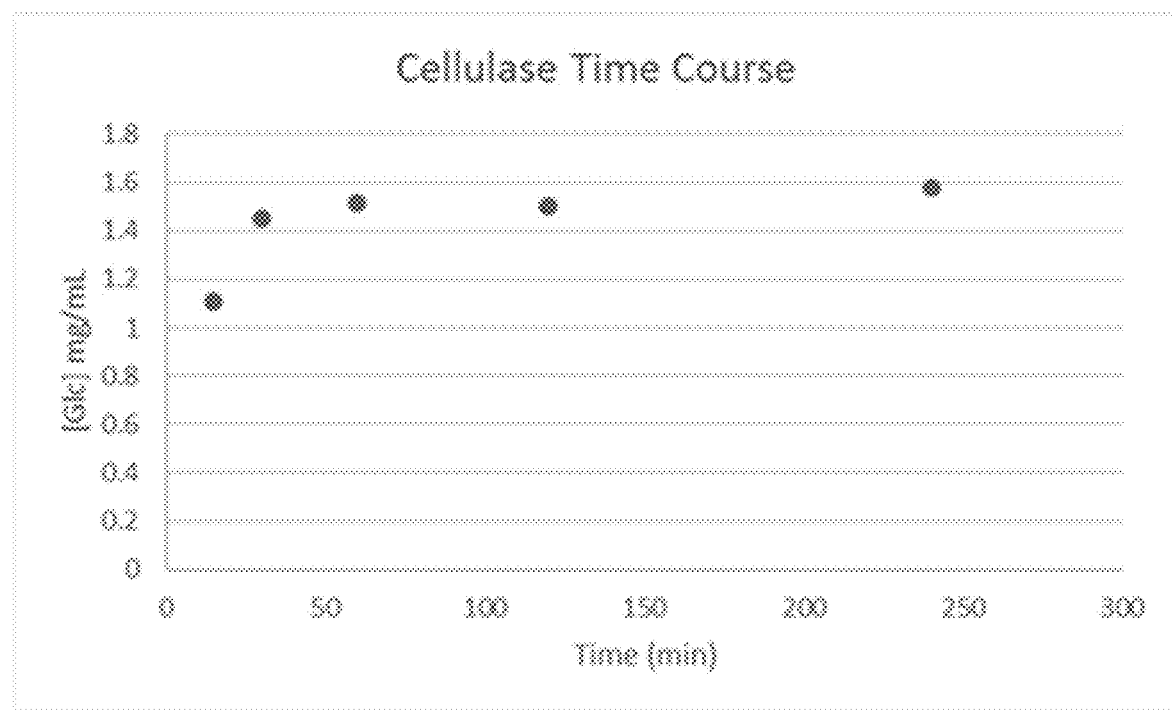
FIG. 4 is a graph of glucose concentrations versus enzymatic saccharification time.

A sample having high cellulose, starch, and glucose concentrations was extracted, and the resulting extractant was subjected to enzymatic hydrolysis using an enzyme cocktail containing cellulase, cellobiohydrolase I and II, and β-glucosidase. The graph of FIG. 4 plots data of glucose concentration over time for this hydrolysis reaction. From the plot it can be seen that the observed concentration of glucose increased from approximately 1 mg/mL to approximately 1.6 mg/mL in its first 125-250 minutes. However, the 1 mg/mL of glucose was seen even in an initial sample taken before hydrolysis could occur. This indicates that a significant amount of glucose was present in the extraction mixture. Because this glucose was not associated with the hydrolysis of cellulose, its presence could interfere with the estimation of initial and extracted cellulose based on observed glucose concentrations after enzymatic hydrolysis.

Example 11. Hydrolysis of Cellulose to Cellobiose

Figure 5:
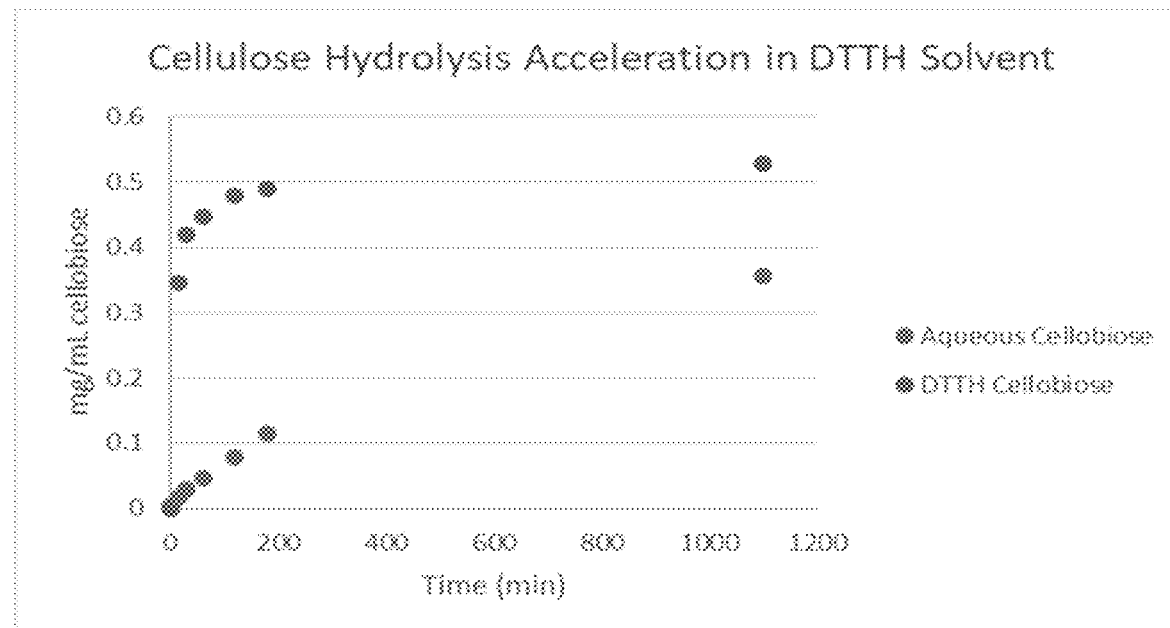
FIG. 5 is a graph of cellobiose concentrations versus enzymatic hydrolysis time following procedures either with or without cellulose extraction using DMSO/TBAF/TBAOH (DTTH).

A sample having high cellulose, starch, and glucose concentrations was extracted, and the resulting extractant was subjected to enzymatic hydrolysis using an enzyme cocktail containing cellulase, cellobiohydrolase I, and cellobiohydrolase II. The graph of FIG. 5 plots data of cellobiose concentration over time for this hydrolysis reaction, either with or without prior extraction with a solution of DMSO, TBAF, and TBAOH, wherein the extraction solution is abbreviated as DTTH. From the plot it can be seen that the sample including the provided extraction protocol exhibited an initial rate of reaction that was accelerated approximately 100-fold relative to that of the comparative sample. Additionally, the extracted sample achieved more than 90% complete conversion to cellobiose within 3 hours, while hydrolysis of the non-extracted sample did not reach 90% conversion before the last analyzed experimental time point.

Example 12. Effect of Selective Precipitation on Cellulose Purity

Standards consisting of cellulose, starch, and glucose concentrations were then extracted as before, but afterwards subjected to a selective precipitation step as described in Example 3. After precipitating the extracted cellulose with a 90% DMSO solution in water having 50 mg/mL sodium perchlorate, and centrifuging, the resultant pellet was rinsed with acetone, suspended, and lyophilized. Acid hydrolysis of the pellets as described in Example 6 was then performed, and the recoveries of the standards were determined. From the results shown in Table 1 below, it can be seen that the selective precipitation precipitated only the cellulose, leaving free glucose and starch in the supernatant. These findings confirmed the ability of the selective precipitation to increase the purity of the extracted cellulose, and reduce interference in subsequent assays caused by the presence of non-cellulosic saccharides.

TABLE 1

|  | Glucose % Recovery | Starch % Recovery | Cellulose % Recovery |
| --- | --- | --- | --- |
| Precipitation 1 | 0 | 0 | 88.7 |
| Precipitation 2 | 0 | 0 | 88.0 |
| Precipitation 3 | 0 | 3.0 | 75.3 |

Example 13. Effect of Peracetic Acid Concentration on Degradation Kinetics

Figure 6:
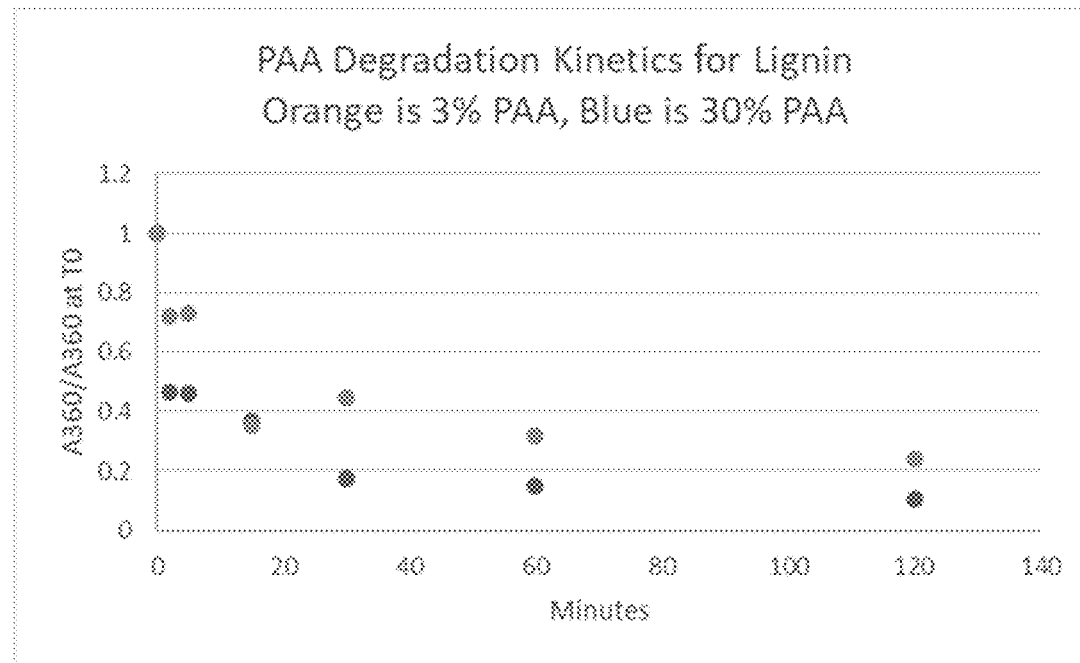
FIG. 6 is a graph of lignin degradation kinetics under peracetic acid pretreatment conditions.
Figure 7:
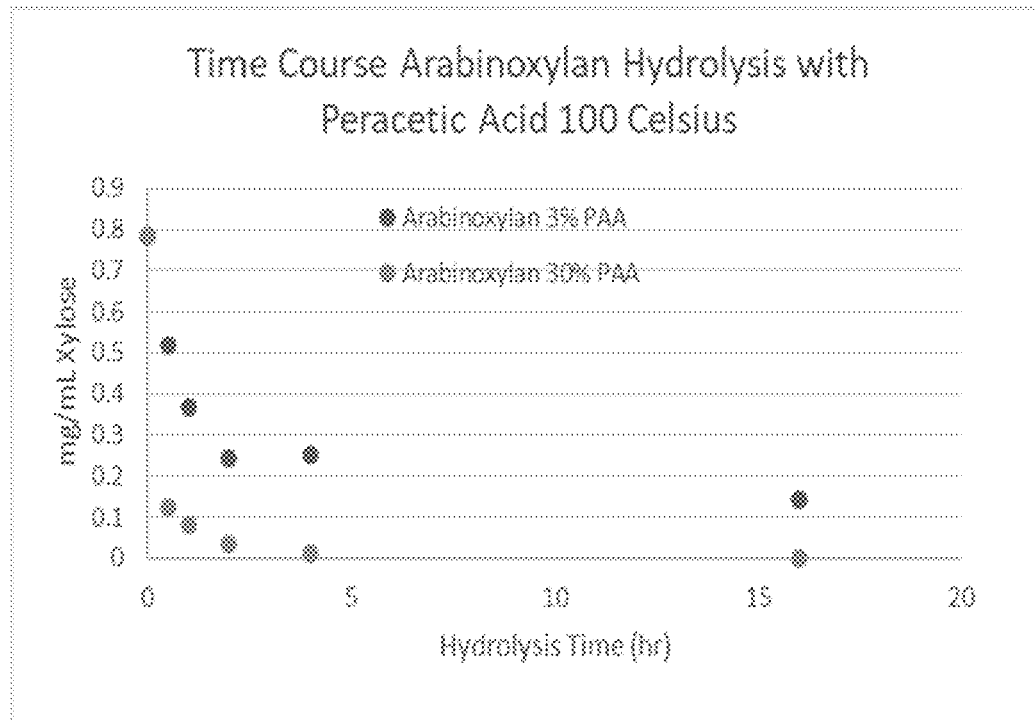
FIG. 7 is a graph of arabinoxylan degradation kinetics under peracetic acid pretreatment conditions.
Figure 8:
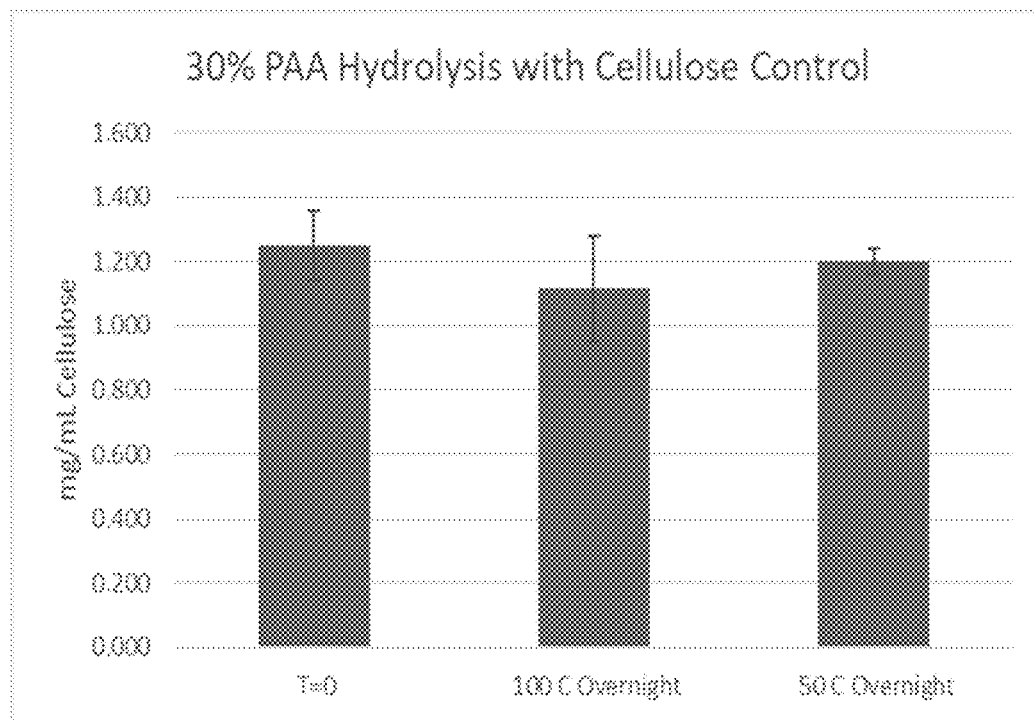
FIG. 8 is a graph of cellulose stability under peracetic acid pretreatment conditions.

The effects of biomass pretreatment with peracetic acid were tested to determine the effectiveness of different pretreatment conditions in degrading lignin and hemicellulose without degrading cellulose. Treatments were carried out in which samples were contacted with peracetic acid to create mixtures having 3% or 30% peracetic acid. These were then aged at either 50° C. or 100° C., and degradation kinetics were observed. The results presented in FIG. 6 show that the 30% peracetic acid mixture was capable of degrading more than 50% of the lignin in the sample within the first few minutes of pretreatment, and more than 90% of the lignin within 2 hours. The results of FIG. 7 show that the 30% peracetic acid mixture was also capable of degrading more than 90% of the arabinoxylan in the sample within 2 hours, as well as almost all of the arabinoxylan within 5 hours. In contrast, from the results of FIG. 8 it can be seen that any effect of the 30% peracetic acid pretreatment on cellulose in the sample is not statistically significant. Together these results demonstrate that relatively harsh peracetic acid conditions can be effectively used to rapidly remove lignin and hemicellulose from biomass samples while leaving the cellulose content of those samples intact.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications, websites, and databases cited herein are hereby incorporated by reference in their entireties for all purposes. Where a conflict exists between the instant application and a reference provided herein, the instant application shall dominate.

What is claimed is:

1. A method of detecting the amount of cellulose in a cellulosic biomass sample, the method comprising:
contacting the cellulosic biomass sample with a solvent mixture, wherein the solvent mixture comprises a polar aprotic solvent, a quaternary ammonium salt, and a quaternary ammonium base, thereby extracting cellulose from the cellulosic biomass sample into the solvent mixture; and
detecting the amount of extracted cellulose.

2. The method of claim 1, wherein the polar aprotic solvent is dimethyl sulfoxide (DMSO).

3. The method of claim 1, wherein the quaternary ammonium salt is tetrabutylammonium fluoride (TBAF).

4. The method of claim 1, wherein the quaternary ammonium base is tetrabutylammonium hydroxide (TBAOH).

5. The method of claim 1, wherein the concentration of the quaternary ammonium salt in the solvent mixture is from 10 mg/mL to 500 mg/mL.

6. The method of claim 1, wherein the concentration of the quaternary ammonium base in the solvent mixture is from 1 mg/mL to 1500 mg/mL.

7. The method of claim 1, wherein the mass ratio of the quaternary ammonium salt to the quaternary ammonium base is from 0.05 to 15.

8. The method of claim 1, wherein the amount of the solvent mixture contacting the cellulosic biomass sample is from 1 mL to 50 mL per gram of cellulosic biomass.

9. The method of claim 1, wherein the detecting comprises:
converting the extracted cellulose into glucose;
measuring a concentration of glucose converted from the extracted cellulose; and
transforming the measured concentration of glucose to a calculated concentration of extracted cellulose.

10. The method of claim 9, wherein the converting of the extracted cellulose into glucose comprises treating the extracted cellulose with one or more saccharifying enzymes.

11. The method of claim 9, wherein the converting of the extracted cellulose into glucose comprises submitting the extracted cellulose to acid hydrolysis.

12. The method of claim 1, wherein the detecting comprises:
converting the extracted cellulose into cellobiose;
measuring a concentration of cellobiose converted from the extracted cellulose; and
transforming the measured concentration of cellobiose to a calculated concentration of extracted cellulose.

13. The method of claim 12, wherein the converting of the extracted cellulose into cellobiose comprises treating the extracted cellulose with one or more saccharifying enzymes.

14. The method of claim 9, further comprising:
prior to the converting, selectively precipitating the extracted cellulose from the solvent mixture.

15. The method of claim 1, wherein the contacting comprises forming cellulose-quaternary ammonium salt complexes in the solvent mixture, and wherein the detecting comprises:
measuring a concentration of cellulose-quaternary ammonium salt complex in the solvent mixture; and
transforming the measured concentration of cellulose-quaternary ammonium salt complex to a calculated concentration of extracted cellulose.

16. The method of claim 15, wherein the measuring comprises a spectroscopic quantification of the cellulose-quaternary ammonium salt complex concentration.

* * * * *